US008324150B2

(12) United States Patent
Chroboczek et al.

(10) Patent No.: US 8,324,150 B2
(45) Date of Patent: Dec. 4, 2012

(54) CELL-PROLIFERATION INHIBITING VPG PROTEINS, FRAGMENTS OR ANALOGS THEREOF AND THEIR APPLICATIONS

(75) Inventors: Jadwiga Chroboczek, Grenoble (FR); Wlodzimierz Zagorski, Varsovie (PL); Renata Grzela, Kielce (PL)

(73) Assignees: Centre National de la Recherche Scientifique, Paris (FR); Institute of Biochemistry and Biophysics—Polish Academy of Sciences, Warsaw (PL); Universite Joseph Fourier, Grenoble Cedex (FR)

( * ) Notice: Subject to any disclaimer, the term of this patent is extended or adjusted under 35 U.S.C. 154(b) by 115 days.

(21) Appl. No.: 12/664,240

(22) PCT Filed: Jun. 13, 2008

(86) PCT No.: PCT/IB2008/002594

§ 371 (c)(1), (2), (4) Date: Feb. 15, 2010

(87) PCT Pub. No.: WO2008/152527

PCT Pub. Date: Dec. 18, 2008

(65) Prior Publication Data

US 2010/0160234 A1 Jun. 24, 2010

(30) Foreign Application Priority Data

Jun. 13, 2007 (EP) .................................... 07290740

(51) Int. Cl.
*A61K 38/00* (2006.01)
*A61K 35/12* (2006.01)

(52) U.S. Cl. ..................................... 514/1.1; 424/277.1
(58) Field of Classification Search ........................ None
See application file for complete search history.

(56) References Cited

U.S. PATENT DOCUMENTS 5,589,612 A 12/1996 Jilka et al.
2006/0294618 A1 * 12/2006 Jahn et al. .................... 800/279

FOREIGN PATENT DOCUMENTS

WO WO 01/40490 6/2001

OTHER PUBLICATIONS

Grzela et al Biochimie 88:887-96, Mar. 2006.*
Benedetti et al, Oncogen 23:3189-3199, 2004.*
Grzela et al Biochimie 88:887-896, 2006.*
International Search Report and Written Opinion from International Patent Application No. PCT/IB2008/002594, filed Jun. 13, 2008.
Database UNIPROTKB/TREMBL; Nov. 1, 1996; Welnicki, M.A. and Baulcombe, D.C.: "The nucleotide sequence of the central fragment of potato virus Y encoding 6K2 and vPg proteins"; XP002450611; Retrieved from EBI; Database accession No. Q85258.
Database EMBL/Genbank/DDBJ; Jan. 24, 1994; Welnicki, M.A. and Baulcombe, D.C.: "Potato virus Y; 6K2 gene"; XP002450612; Retrieved from EBI; Database accession No. Z29526; Cited in Application.
Grzela R et al: "Polyvirus terminal protein VPg, effector of host eukaryotic initiation factor eIF4E"; BIOCHIMIE (Paris); vol. 88, No. 7; Jul. 2006; pp. 887-896; XP005595433.

* cited by examiner

*Primary Examiner* — Lei Yao
(74) *Attorney, Agent, or Firm* — Alston and Bird LLP

(57) ABSTRACT

Use of VPg proteins, fragments or analogs thereof having the ability to bind an eukaryotic initiation factor eIF4E, for inhibiting cell-proliferation.

10 Claims, 8 Drawing Sheets

Increase in tumor size (fold)

| | | |
|---|---|---|
| 1,65-3,59 | 1,46-3,64 | 1-1,63 |

CELL-PROLIFERATION INHIBITING VPG PROTEINS, FRAGMENTS OR ANALOGS THEREOF AND THEIR APPLICATIONS

CROSS REFERENCE TO RELATED APPLICATIONS

This application is a national stage application filed under 35 U.S.C. 371 of International Application No. PCT/IB2008/002594, filed Jun. 13, 2008, which claims priority from European Application No. 07290740.5, filed Jun. 13, 2007.

FIELD AND BACKGROUND OF THE INVENTION

The present invention relates to the field of cell proliferation-inhibiting proteins. More particularly, the invention relates to a protein comprising or consisting of a VPg protein, fragments thereof or analogs thereof, that are cytotoxic to eukaryotic cells, and/or inhibit the cell proliferation. The invention also relates to medical uses of such a protein, fragments thereof or analogs thereof.

Eukaryotic initiation factor eIF4E is a mRNA 5' cap-binding protein, which both attaches mRNA and binds the eIF4G component of the eIF4F initiation complex. A significant fraction of eIF4E (up to nearly 70%) localizes to the nucleus (Lejbkowicz et al., 1992). It has been shown that nuclear eIF4E is involved in the nucleocytoplasmic transport of certain messenger RNAs (Lejbkowicz et al., 1992; Rosenwald et al., 1995; Rousseau et al., 1996; Lai and Borden, 2000). It has been demonstrated that the unchecked over-expression of eIF4E can cause cell growth and malignant transformation, whereas reduction of the eIF4E level can reverse the transformed phenotype (reviewed in Sonenberg and Gingras, 1998). Furthermore, in humans, some tumor types exhibit elevated levels of eIF4E (Ruggero and Pandolfi, 2003). It appears that at high eIF4E levels there is increased cytoplasmic level of proteins involved in the malignant transformation, due to the increase in the eIF4E-dependent transport of the appropriate mRNAs to the cytoplasm (Shantz and Pegg, 1994; Rousseau et al., 1996; Lai and Borden, 2000).

International Application No. WO 00/78803 describes eIF4E- binding peptides useful in therapy, and particularly for the induction of programmed cell death, presumably by disrupting the formation of the eIF4F complex. All these peptides comprise the amino acid sequence (motif) YxxxxLØ (SEQ ID NO: 31), wherein x is any amino acid and Ø is Leu, Met or Phe, required for binding human eIF4E (accession number NP_001959 in the GENBANK database, Apr. 15, 2007 version).

Thus, there is an interest in the development of adequate eIF4E binding agents for use in anti-cancer therapy. There is also a need to find eIF4E binding agents possessing a distinct mechanism of action from that described above, to overcome drug resistances for instance.

Potato virus Y (PVY) is the type member of the Potyvirus genus, belonging to the Potyviridae family, the largest and economically most important group of plant viruses. Potyviruses have a so-called genome-linked VPg protein (hereinafter referred to as VPg protein or VPg) covalently attached to the 5' end of their linear nucleic acid genomes (Riechmann et al., 1989 and Murphy et al., 1991). The potyvirus VPg protein is implicated in virus protein synthesis, long-distance movement in plant tissue and virus replication (Lellis et al., 2002; Schaad et al., 2002; Fellers et al., 1998). Early after potyvirus infection, the genomic RNA interacts with the host cellular machinery to initiate protein synthesis. The VPg protein seems to play an important role in this early event, because removal of VPg protein with proteinase K from the genomic RNA abolishes RNA infectivity and, in addition, decreases its translation efficiency in vitro (Leonard et al., 2000; Herbert et al., 1997). The amino acid sequence of the potato virus Y genome-linked protein VPg corresponds to the amino acid residues 336 to 523 of the amino acid sequence identified under accession number CAA82642 in the GENBANK database (Nov. 14, 2006 version). It is reproduced herein as SEQ ID NO: 2.

Recent studies have reported an interaction between the VPg protein of certain potyviruses (turnip mosaic virus, lettuce mosaic virus, tobacco vein mottling virus, potato virus Y) and the plant translation initiation factor eIF4E (Wittmann et al., 1997; Duprat et al., 2002; Kang et al., 2005; Grzela et al., 2006). It has also been shown that the VPg protein encoded by certain vertebrate viruses of the Caliciviridae family, such as the feline calcivirus (FCV), the lordsdale virus (LDV)) or the recently discovered murine norovirus (MNV-1) interact with the cap-binding protein eIF4E (Goodfellow et al., 2005; Chaudhry et al., 2006).

Grzela et al. (2006) have found that the interaction between PVY VPg protein and eIF4E seems to have rather low species specificity since it was also observed with yeast as well as with the insect (S. frigiperda) eIF4Es. The authors have also described that the VPg/eIF4E interaction results in some inhibition of cell-free protein synthesis in insect cells, but without leading to insect cell death. However, the PVY VPg primary amino acid sequence does not exhibit the eIF4E-binding motif YxxxxLØ SEQ ID NO: 31) described above.

SUMMARY OF THE INVENTION

Now, the Inventors have observed that, in presence of potato virus Y VPg protein, the nuclear pool of eIF4E was dramatically depleted in human cells. Thus and surprisingly, the Inventors have shown that the VPg protein immobilizes human initiation factor eIF4E in the cytoplasm, which results, contrary to what was observed previously in insect cells, in the inhibition of cell proliferation, leading to cell death.

Therefore, in a first aspect, the present invention relates to an isolated and purified protein comprising or consisting of a VPg protein or a fragment thereof of at least 8 amino acids or an analog thereof:

(i) having the ability to bind an eukaryote initiation factor eIF4E, preferably a mammal initiation factor eIF4E and more preferably a human initiation factor eIF4E, and (ii) said protein, fragment thereof or analog thereof not comprising the amino acid motif YxxxxLØ(SEQ ID NO: 31), wherein x is any amino acid, Y is tyrosine (Tyr), L is leucine (Leu) and Ø is leucine (Leu), methionine (Met) or phenylalanine (Phe), as a medicament, preferably as an anti-cancer agent, or for use in treating cancer, preferably glioma, melanoma or a colon or lung cancer, in which the cancer cells express, preferably over-express, the initiation factor eIF4E, in a subject.

A "subject" refers to a mammal, preferably a human.

The characterization of the binding (or interaction) of a protein, a fragment thereof or an analog thereof according to the present invention to an eukaryotic (e.g., insect), preferably a mammal and more preferably a human eIF4E can be performed by an ELISA-based binding assay as described in Grzela et al. (2006). Advantageously, the dissociation constant between said protein, fragment thereof or analog thereof and said eIF4E is between about 5 nM and about 450 nM. Dissociation constant (or affinity) measurements may be made using methods known to those skilled in the art, including using the method described in Grzela et al. (2006).

Optionally, this characterization may be combined with the in vitro determination of the change in cellular localization of eIF4E (immobilization of eIF4E in the cytoplasm) in the presence of a protein, a fragment thereof or an analog thereof of the present invention, in eukaryotic, preferably mammal and more preferably human cells. By way of example, the in vitro determination of the change in cellular localization of eIF4E in the presence of a protein, a fragment thereof or an analog thereof of the present invention can be performed in insect cells (e.g., High Five (*Trichoplusia ni*) cells), since these cells are a good predictive model for said determination in human cells. This determination can be performed as in Examples 3 or 4 below.

The terms "protein" and "peptide" may be used interchangeably herein. They are well known in the art and refer to a polymeric form of amino acids of any length. The terms also refer to a protein or peptide comprising chemically or biochemically modified amino acids, as well as a protein or peptide having modified peptide backbones, e.g. a protein or peptide containing one or more modifications to L-amino acid side-chains (for example D-amino acids), or to the alpha-amino acid backbone.

A VPg protein, according to the present invention, refers usually to a virus-encoded protein covalently attached to the 5' end of the linear nucleic genome of said virus (Riechmann et al., 1989 and Murphy et al., 1991), and also comprises according to the present invention:

an isolated plant virus-encoded VPg protein, a recombinant VPg protein of a plant virus, or a synthetic VPg protein of a plant virus.

Preferably, said VPg protein consists of about 188 to 193 amino acid residues and includes the amino acid motif KGK and NMYG (SEQ ID NO: 26).

In a preferred embodiment, the VPg protein is the potato virus Y-encoded VPg protein of SEQ ID NO: 2.

The term "plant virus" refers to a virus capable of spreading through a plant and particularly of infecting at least one type of plant cells.

In another embodiment of the present invention, the VPg protein analog is an analog of PVY VPg protein of SEQ ID NO: 2, exhibiting at least 20%, and by order of increasing preference, at least 25%, 30%, 35%, 40%, 45%, 50%, 55%, 60%, 65%, 70%, 75%, 80%, 85%, 90%, 95%, 98% or 99% sequence identity, or at least 45%, and by order of increasing preference, at least 50%, 55%, 60%, 65%, 70%, 75%, 80%, 85%, 90%, 95%, 98% or 99% sequence similarity with the full-length of PVY VPg protein of SEQ ID NO: 2, provided that said VPg protein analog still has the ability to bind an eukaryote (e.g., insect) initiation factor eIF4E, preferably a mammal initiation factor eIF4E and more preferably a human initiation factor eIF4E as described above.

Examples of VPg protein analogs are VPg proteins encoded:

by other plant virus than the PVY, preferably belonging to the Potyviridae family, more preferably to the Potyvirus genus, such as the tobacco etch virus (TEV) (SEQ ID NO: 4), the clover yellow vein virus (C1YVV) (accession number NP_734169.1 in the GENBANK database, Mar. 30, 2006, version, reproduced herein as SEQ ID NO: 6), the tobacco vein mottling virus (TVMV) (accession number NP_734333.1 in the GENBANK database, Mar. 30, 2006, version, reproduced herein as SEQ ID NO: 8), the turnip mosaic virus (TuMV) (SEQ ID NO: 10), the lettuce mosaic virus (LMV) (accession number NP_734159.1 in the GENBANK database, Mar. 30, 2006, version, reproduced herein as SEQ ID NO: 12), or by a virus belonging to the Calcivirus family, preferably to the Norovirus genus, such as the feline calicivirus (FCV) (accession number Q66914 in the UniProtKB/Swiss-Prot database, reproduced herein as SEQ ID NO: 27), human norovirus (HuNoV, accession numbers P54634 in the UniProtKB/Swiss-Prot database, and NP_056820 in the GENBANK database, reproduced herein as SEQ ID NO: 28 and 29 respectively) and murine norovirus (MNV) (accession number YP_720001 in the GENBANK database, reproduced herein as SEQ ID NO: 30).

According to another embodiment of the present invention, the fragment of a protein as defined above is a fragment of a VPg protein or a fragment of a protein analog of a VPg protein as defined here above, comprising or consisting of at least 8, and by order of increasing preference at least 10, 15, 20, 25, 26 or 42 contiguous amino acids residues of said VPg protein or said analog thereof, but that retains the ability to bind an eukaryote (e.g., insect) initiation factor eIF4E, preferably a mammal initiation factor eIF4E and more preferably a human initiation factor eIF4E, as described above.

By way of example, the fragment as defined above comprises or consists of at least 8, and by order of increasing preference at least 10, 15, 20, 25, 26 or 42 contiguous amino acids residues of the amino acid sequence of any of the VPg protein as defined here above, preferably of SEQ ID NO: 2, 4, 6, 8, 10 or 12.

In another preferred embodiment of the present invention, the fragment of PVY VPg (SEQ ID NO: 2) comprises or consists of the amino acid sequence located:

between the arginine (Arg) at position 41 and the arginine (Arg) at position 94 (also named VPg2; SEQ ID NO: 14) of SEQ ID NO: 2, or between the arginine (Arg) at position 41 and the glycine (Gly) at position 82 (also named VPg4; SEQ ID NO: 16) of SEQ ID NO: 2, between the arginine (Arg) at position 41 and the phenylalanine (Phe) at position 66 (also named VPg5; SEQ ID NO: 18) of SEQ ID NO: 2, between the arginine (Arg) at position 41 and the arginine (Arg) at position 59 (also named VPg1; SEQ ID NO: 20) of SEQ ID NO: 2, or between the phenylalanine (Phe) at position 60 and the arginine (Arg) at position 94 (also named VPg3; SEQ ID NO: 22) of SEQ ID NO: 2.

In another embodiment, the fragment comprises or consists of at least 8, and by order of increasing preference at least 10, 15, 20, 25 or 26 contiguous amino acids residues of the amino acid sequence SEQ ID NO: 16.

In another embodiment, the fragment of the VPg protein consists of an analog of SEQ ID NO: 16 exhibiting at least 60%, and by order of increasing preference, at least 65%, 70%, 75%, 80%, 85%, 90%, 95%, 98% or 99% sequence identity, or at least 80%, and by order of increasing preference, at least 85%, 90%, 95%, 98% or 99% sequence similarity with the full-length of amino acid sequence of SEQ ID NO: 16.

In another embodiment, the fragment of the VPg protein consists of an analog of SEQ ID NO: 18 exhibiting at least 60%, and by order of increasing preference, at least 65%, 70%, 75%, 80%, 85%, 90%, 95%, 98% or 99% sequence identity, or at least 80%, and by order of increasing preference, at least 85%, 90%, 95%, 98% or 99% sequence similarity with the full-length of amino acid sequence of SEQ ID NO: 18.

The term "analog" is intended to encompass any form of PVY VPg protein (SEQ ID NO: 2) or a fragment thereof (e.g., SEQ ID NO: 16 or SEQ ID NO: 18) as defined here above, wherein one or more of the amino acids within the amino acid sequence has been replaced with an alternative amino acid or another residue such as a carbohydrate, a lipid or a chemical and/or wherein one or more of the amino acids has been deleted or wherein one or more additional amino acids or another residue such as a carbohydrate, a lipid or a chemical has been added to the peptide chain or amino acid sequences of PVY VPg protein or a fragment thereof, provided that said analog still has the ability to bind an eukaryote (e.g., insect) initiation factor eIF4E, preferably a mammal initiation factor eIF4E and more preferably a human initiation factor eIF4E, as described above.

Many suitable computer programs for calculating the "identity" between two amino acid sequences are generally known in the art, such as BLAST program, choosing the scoring matrix BLOSUM62.

The term "similarity" refers to a comparison of the amino acid residues of two peptides wherein conservative amino acid residue substitutions are permitted, i.e. amino acid residues that share the same charge and the same polarity are considered similar. The conservative changes do not significantly alter the binding characteristics of the resulting peptide. The following is one example of various groupings of amino acids:

Amino Acids with Nonpolar R Group

Alanine, Valine, Leucine, Isoleucine, Proline, Plenylalanine, Tryptophan, Methionine.

Amino Acids with Uncharged Polar R Groups

Glycine, Serine, Threonine, Cysteine, Tyrosine, Asparagine, Glutamine.

Amino Acids with Charged Polar R Groups (Negatively Charged at pH 6.0)

Asapartic acid, Glutamic acid

Basic Amino Acids (Positively Charged at pH 6.0)

Lysine, Arginine, Histidine (at pH 6.0)

Amino Acids with OH Group

Serine, Threonine, Tyrosine

Amino Acids with an Aromatic Group

Phenylalanine, Tyrosine, Tryptophan

Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asaparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred conservative substitutions are:

Lysine for Arginine and vice versa such that a positive charge may be maintained;

Glutamic acid for Aspartic acid and vice versa such that a negative charge may be maintained;

Serine for Threonine such that a free —OH can be maintained;

Tyrosine for Phenylalanine such that the aromatic character of the residue can be maintained; and Glutamine for Asparagine such that a free —$NH_2$ can be maintained.

The sequence similarity values provided herein are determined as described above in reference to calculation of sequence identity.

Optionally, the protein, fragment thereof or analog thereof as defined here above may comprise an amino acid sequence facilitating cellular uptake. Such amino acid sequences, known as Cell Penetrating Peptides, are well known in the art; See CELL PENETRATING PEPTIDES: PROCESSES AND APPLICATIONS, edited by Ulo Langel (2002); or Advanced Drug Delivery Reviews, 2005, 57:489-660). These include the Human Immunodeficency Virus type 1 (HIV-1) protein Tat or fragment thereof (Ruben et al., 1989), the herpes virus tegument protein VP22 (Elliott and O'Hare, 1997), penetratin (Derossi et al., 1996), protegrin 1 anti-microbial peptide SynB (Kokryakov et al., 1993) and the basic fibroblast growth factor (Jans, 1994).

A second aspect of the present invention relates to the use of a protein, a fragment thereof or an analog thereof as defined here above for the manufacture of a medicament for treating cancer, preferably glioma, melanoma or a lung or colon cancer, in which the initiation factor eIF4E is expressed or overexpressed, in a subject.

In a third aspect, the present invention provides an isolated nucleic acid sequence encoding a protein, a fragment thereof or an analog thereof as defined above. The nucleic acid sequence of the invention can be synthesized using standard techniques. Techniques for nucleic acid manipulation are known in the art (See, for example, in Sambrook J. et al. (2000) Molecular Cloning: A Laboratory Manual). By way of example, the nucleic acid sequence comprises or consists of the nucleic acid sequences SEQ ID NO: 1 (residues 1007 to 1570 of the nucleotide sequence identified under accession number Z29526 in the GENBANK database (Nov. 14, 2006 version) encoding PVY VPg protein), or SEQ ID NO: 3, 5, 7, 9, 11, 13, 15, 17, 19 or 21.

The present invention also provides a recombinant vector for the expression of a protein, a fragment thereof or an analog thereof as defined above. The recombinant vector comprises at least one nucleic acid sequence encoding a protein, a fragment thereof or an analog thereof as defined above, operably linked to at least one regulatory sequence.

The term "vector" is intended to mean a nucleic acid molecule capable of transporting another nucleic acid. By way of example, a vector which can be used in the present invention includes, but is not limited to, a viral vector (e.g., retrovirus, adenovirus, baculovirus), a plasmid, a RNA vector or a linear or circular DNA or RNA molecule which may consist of a chromosomal, non chromosomal, semi-synthetic or synthetic nucleic acid. Large numbers of suitable vectors are known to those of skill in the art and commercially available. Preferred vectors are those capable of autonomous replication (episomal vector) and/or expression of nucleic acids to which they are operably linked (expression vectors).

The term "operably linked" is intended to mean that the nucleotide sequence is linked to a regulatory sequence in a manner which allows expression of the nucleotide sequence.

The term "regulatory sequence" includes promoters, enhancers and transcriptional or translational control elements. Such regulatory sequences are also known in the art.

By way of example, expression vectors may include an origin of replication or autonomously replicating sequence (ARS) and expression control sequences, a promoter, an enhancer and necessary processing information sites, such as ribosome-binding sites, RNA splice sites, polyadenylation sites, transcriptional and translational terminator sequences, and mRNA stabilizing sequences. Such vectors may be prepared by means of standard recombinant techniques well known in the art and discussed, for example, in Sambrook et al., 2000.

The present invention also relates to the use of at least one recombinant vector expressing a nucleic acid encoding a protein, a fragment thereof or an analog thereof as defined above, for the preparation of a medicament for preventing or treating cancer.

The expression vector according to the present invention can also be used to transfect or transduct (e.g., by electroporation) or infect cells to thereby introduce or produce a protein, a fragment thereof or an analog thereof as defined above.

The present invention further relates to a host cell transfected to express a protein, a fragment thereof or an analog thereof as defined above. The host cell can be transfected with the nucleic acid or the vector of the present invention. The host cell may be any procaryotic or eucaryotic cell. For example, a protein, a fragment thereof or an analog thereof as defined above may be expressed in bacterial cells such as *E. coli*, insect cells, yeast, mammalian cells such as Chinese hamster ovary cells (CHO) or animal or human cells such as B16, LGL26, HeLa or 293 or any transformed cell line.

In another aspect, the present invention provides a pharmaceutical composition comprising a protein, a fragment thereof or an analog thereof or a recombinant vector as defined here above and a pharmaceutically acceptable carrier. The composition according to the present invention is useful for treating cancer, preferably glioma, melanoma or a colon or lung cancer, in which the initiation factor eIF4E is expressed or over-expressed, in a subject.

As used herein, "pharmaceutically acceptable carrier" is intended to include any and all solvents, dispersion media, liposomes, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Cationic lipids, nonaqueous vehicles such as fixed oils and commercially available transductants may also be used. The use of such media and agents for pharmaceutically active substances is well known in the art. Except insofar as any conventional media or agent is incompatible with a protein, a fragment thereof or an analog thereof as defined hereabove, use thereof in the composition of the present invention is contemplated.

By way of example, when the pharmaceutical composition comprises a protein, a fragment thereof or an analog thereof, then the pharmaceutically acceptable carrier is preferably a cationic lipid, or a mixture of non-cationic lipids and a cationic lipid.

In yet another aspect, the present invention comprises a method of inhibiting cancer cell proliferation, characterized in that said method comprises the step of treating a subject in need thereof with a composition comprising a protein, a fragment thereof or an analog thereof as defined here above.

The term "inhibiting" refers to slowing, decreasing, delaying, preventing or abolishing cell proliferation.

The term "cell proliferation" refers to the rate at which a group of cells divides. The number of cells growing can be easily quantified by one skilled in the art.

The term "cancer" refers to any of a number of diseases that are characterized by uncontrolled, abnormal proliferation of cells, the ability of affected cells to spread locally or through the bloodstream and lymphatic system to other parts of the body (i.e., metastases), as well as any of a number of characteristic structural and/or molecular features. Examples of cancers are breast, colorectal, liver, lung (such as small cells, non-small cells), bronchic, prostate, ovarian, brain, pancreatic, colon, head and neck, stomach and bladder cancers, non-Hodgkin's lymphomas, melanomas, leukaemias, neuroblastomas, gliomas, or glioblastomas.

A "cancer cell" is understood as a cell having specific structural properties, which can lack differentiation and be capable of invasion and metastasis. Preferably, the cancer cells express or over-express the initiation factor eIF4E. Cancer cells expressing eIF4E can be identified by methods known in the art, e.g., by DNA sequencing, or by Northern blot, or by immunochemistry using anti-eIF4E antibodies.

The term "over-express" means that the gene encoding eIF4E protein is expressed at a higher level compared to the one of a normal (i.e., non cancer cell) quiescent eukaryotic, mammal or human cell, resulting in the production in a cancer cell with eIF4E level exceeding the one normally produced in said normal cell. The normal range of expression or production can be determined by routine methods as by assaying the eIF4E protein, its mRNA, or its gene.

The term "treating" includes the administration of the protein, a fragment thereof or an analog thereof as defined here above, or a composition of the present invention, to a patient who has a disease or disorder (e.g., cancer or metastatic cancer), a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease, or extend duration of life.

In another aspect, the present invention relates to the use of an isolated and purified initiation factor eIF4E, preferably from human origin, to screen for compounds (e.g., drugs) that mimic the binding specificity of a VPg protein, preferably the VPg protein of SEQ ID NO: 2, with eIF4E.

In another aspect the present invention relates to a method of screening for compounds (e.g., drugs) which mimic the binding specificity of a VPg protein, preferably of SEQ ID NO: 2, 4, 6, 8, 10 or 12, and more preferably of SEQ ID NO: 2, with the initiation factor eIF4E (preferably the human eIF4E), comprising the steps of i) contacting an isolated and purified eIF4E with a candidate compound and a protein, a fragment thereof or an analog thereof according to the present invention (e.g., SEQ ID NO: 2) and ii) detecting if this candidate compound inhibits the binding (or interaction) between eIF4E and said protein, a fragment thereof or an analog thereof. Standard methods are available in the art to carry out competitive binding assays. In addition, the detection of the binding (or interaction) of a peptide compound with eIF4E can be carried out as described in Grzela et al. (2006).

Candidate compounds include peptides such as soluble peptides, lipids, carbohydrates, lipopeptides, glycopeptides, and small organic and inorganic molecules.

The Table 1 below sums up the nucleic acid and peptide sequences used in the present description.

| SEQ ID NO: | Description of the sequence |
|---|---|
| 1 | nucleic acid sequence encoding PVY VPg protein |
| 2 | PVY VPg protein |
| 3 | nucleic acid sequence encoding TEV VPg protein |
| 4 | TEV VPg protein |
| 5 | nucleic acid sequence encoding ClYVV VPg protein |
| 6 | ClYVV VPg protein |
| 7 | nucleic acid sequence encoding TVMV VPg protein |
| 8 | TVMV VPg protein |
| 9 | nucleic acid sequence encoding TuMV VPg protein |
| 10 | TuMV VPg protein |
| 11 | nucleic acid sequence encoding LMV VPg protein |
| 12 | LMV VPg protein |
| 13 | nucleic acid sequence encoding VPg2 |
| 14 | VPg2: amino acid sequence located between the arginine (Arg) at position 41 and the arginine (Arg) at position 94 of SEQ ID NO: 2 |
| 15 | nucleic acid sequence encoding VPg4 |
| 16 | VPg4: amino acid sequence located between the arginine (Arg) at position 41 and the glycine (Gly) at position 82 of SEQ ID NO: 2 |
| 17 | nucleic acid sequence encoding VPg5 |
| 18 | VPg5: amino acid sequence located between the arginine (Arg) at position 41 and the phenylalanine (Phe) at position 66 of SEQ ID NO: 2 |
| 19 | nucleic acid sequence encoding VPg1 |
| 20 | VPg1: amino acid sequence located between the arginine (Arg) at position 41 and the arginine (Arg) at position 59 of SEQ ID NO: 2 |
| 21 | nucleic acid sequence encoding VPg3 |
| 22 | VPg3: amino acid sequence located between the phenylalanine (Phe) at position 60 and the arginine (Arg) at position 94 of SEQ ID NO: 2 |
| 23 | PVY VPg gene forward primer |
| 24 | PVY VPg gene reverse primer |
| 25 | polyhedrin promotor of AcMNPV |
| 26 | VPg motif NMYG |
| 27 | FCV VPg protein |
| 28 | HuNoV VPg protein |
| 29 | HuNoV VPg protein |
| 30 | MNV VPg protein |
| 31 | YxxxxLΦ peptide motif |

BRIEF DESCRIPTION OF THE DRAWINGS

In addition to the preceding features, the invention further comprises other features which will emerge from the following description, which refers to examples illustrating the present invention, as well as to the appended figures.

In FIG. 1A the HeLa cells were not transduced.

EXAMPLES

Example 1

Materials and Methods

Figure 1:
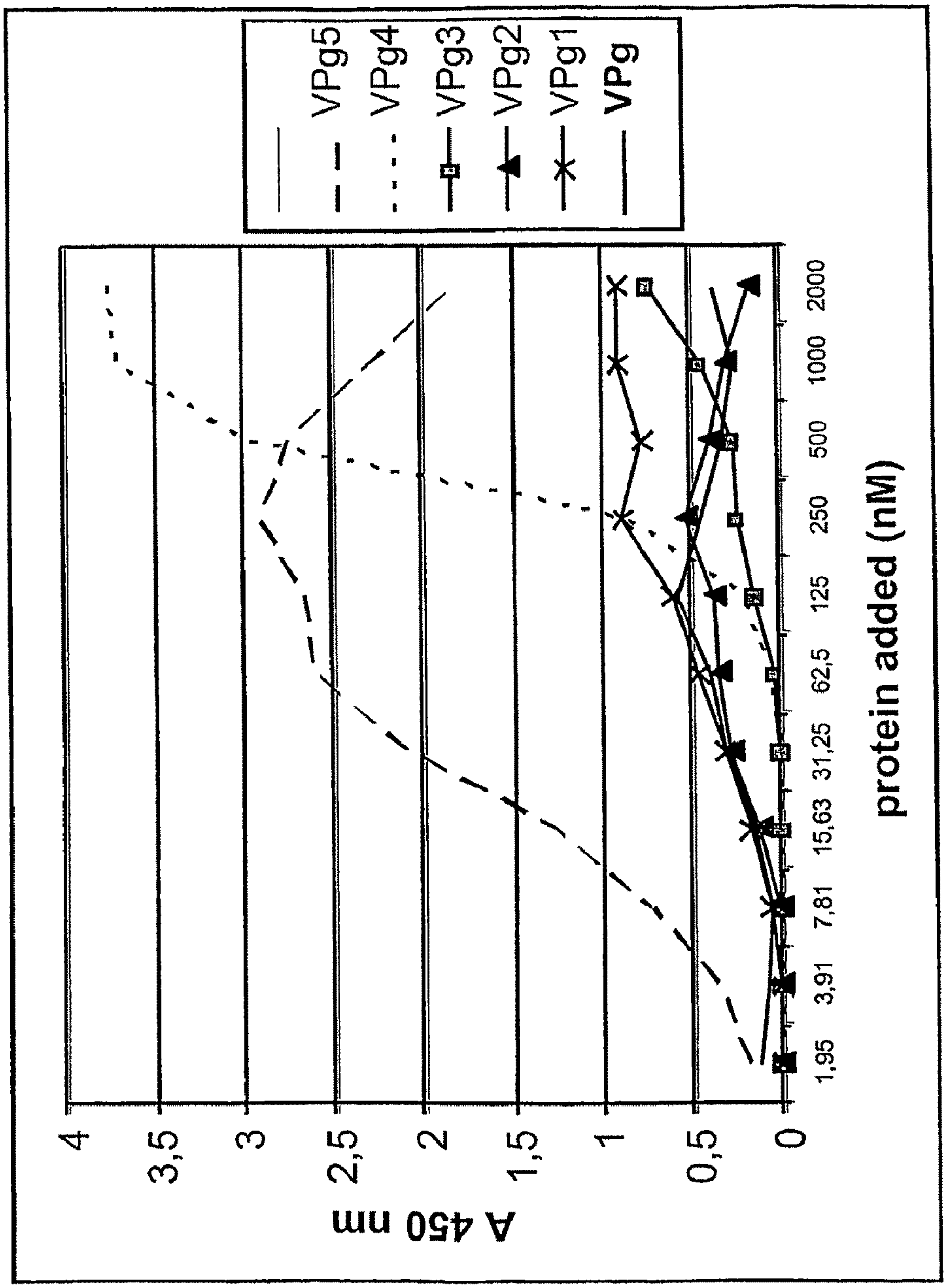
FIG. 1: Interaction assay between human eIF4E and PVY VPg protein or fragments thereof (VPg1 to VPg4).

Cells.

High-Five insect (*Trichoplusia ni*) cells grown in suspension were cultured in Express Five SFM medium (Invitrogen) with gentamicin (50 mg/ml) and amphotericin B (0.25 mg/ml).

HeLa (human cervix carcinoma), B16-ova (mouse melanoma), GL26 (mouse glioma), IMR90 (human primary diploid fibroblasts) were grown in DMEM+GlutaMAX™-I (Gibco) medium complemented with 10% FCS.

Antibodies. Anti-his mouse monoclonal antibody (MMS-156P) was purchased from BabCO (Berkeley, Calif., USA). Anti-eIF4E mouse monoclonal (P-2; sc-9976) was from Santa Cruz Biotechnology (Santa Cruz, Calif., USA). It recognizes mouse, rat, human and porcine eIF4E. Anti-eIF4E rabbit polyclonal antibody against human eIF4E (purchased from Jackson ImmunoResearch Laboratories) was kind gift of Nahum Sonenberg (McGill University, Montreal Canada).

Anti-VPg rabbit polyclonal antibody was prepared in Elevage Scientifique des Dombes (Chatillon, France), using as antigen PVY hisVPg expressed in baculovirus (described below) and was affinity purified to VPg as follows. First an acetone powder obtained from 1 g of non-infected insect cells was used to remove cross-reacting antibodies from serum. Cell powder was added to the anti-VPg rabbit serum up to final concentration of 1%, and stored on ice overnight with gentle rolling. After centrifugation at 10 000 g for 10 min at 4° C., supernatant fraction was applied to CNBr-activated Sepharose 4B (purchased from Amersham Bioscience) containing VPg protein immobilized according to the manufacturers instructions. Bound antibody was eluted with 100 mM glycine pH 2.4 directly into tubes containing 30 μl of 3 M Tris, pH 8.8 and 20 μl 5 M NaCl.

Recombinant protein expression and purification. VPg gene of potato virus Y (strain O, accession number Z29526 in GENBANK database) was synthesized by PCR using plasmid pPVY15 (available under accession number Z29526 in GENBANK database, Nov. 14, 2006 version) as template, with the forward primer 5' GGGGGGGATCCATGGG-GAAAATAAA-3' (SEQ ID NO: 23) and the reverse primer 5' CCCCCAGATCTCTATTATTCATGCTCC-3' (SEQ ID NO: 24, permitting the expression of the protein with the accession number CAA82642 in the GENBANK database. VPg cDNA was inserted into pFastBac HTb (purchased from Invitrogen, Carlsbad, Calif., USA) under the control of polyhedrin promotor (SEQ ID NO: 25) of AcMNPV (O'Reilly et al., 1992) and the recombinant baculovirus expressing his-tagged VPg was constructed using bacmid technology (purchased from Gibco BRL). The High Five (*Trichoplusia ni*) cells in suspension were infected with the recombinant baculovirus at MOI of 5 pfu/cells. Portion (100 ml) of recombinant baculovirus-infected HF cells was collected at 72 h p.i. suspended in 10 ml of 50 mM phosphate buffer, pH 7.0, containing 300 mM NaCl, 6 mM β-mercaptoethanol, 5% glycerol, 0.5% Tween 20 and protease inhibitor cocktail (Complete, purchased from Roche) and lysed by five cycles of freezing in liquid nitrogen and thawing at 37° C. After clearing the extract was passed by gravity through 1 ml of Ni-NTA agarose resin (purchased from Qiagen), equilibrated with 5 ml of lysis buffer. Bound proteins were eluted 5×500 μl of 250 mM imidazole in the 50 mM phosphate buffer, pH 7.0, containing 300 mM NaCl. Fusion tag was removed from VPg with TEV protease for 48 h incubation at 10° C. The resulting products were purified on 5 ml Hi-Trap Heparin column (purchased from Amersham Pharmacia). Proteins were applied on the column in 100 mM NaCl in 50 mM phosphate, pH 7.0, washed with the same buffer until the $OD_{280}$ reached stable level and then eluted in the gradient of NaCl in 50 mM phosphate, pH 7.0 (from 100 mM to 1 M). The fractions containing full-length hisVPg were collected, diluted and fractionated on 5 ml 15 S-Source column (purchased from Amersham Pharmacia) under conditions used for Hi-Trap Heparin column. His-tagged domain II of HCV helicase was expressed in HF cells after infection with the appropriate baculovirus at MOI 5 and purified as described (Boguszewska-Chachulska et al., 2004). All steps were analyzed on 12% SDS-PAGE by staining with CBB, using Precision Plus Protein Dual Colour (purchased from Bio-Rad) and BenchMark Prestained Protein Ladder (purchased from Invitrogen) as molecular weight standards.

Cell fractionation. High Five (*T. ni*) cells at the concentration $2\times10^6$ cells/ml were infected with the baculoviruses expressing VPg protein or hisVPg, or domain II of HCV helicase or empty bacmid, at MOI 5. The infected cells were collected at the indicated times p.i. by centrifugations at 2000 rpm for 10 min. The pellets were washed twice in PBS and resuspended in four times the packed cell volume of hypotonic buffer (10 mM Tris, pH 7.9, 10 mM KCl, 3 mM DTT, 0.1 mM EDTA, 0.1 mM EGTA, 0.75 mM spermidine, 15 mM spermine). The cells were allowed to swell on ice for 30 min and checked with phase microscope for complete breakage. Then a 1/10 volume of restoration buffer (50 mM Tris, pH 7.9, 0.75 mM spermidine, 0.15 mM spermine, 10 mM KCl, 0.2 mM EDTA, 3 mM DTT, 67.7% sucrose) was added and the homogenate was layered over a 1 ml of sucrose cushion (30% sucrose in hypotonic buffer) and centrifuged in cold for 20 min at 3000 rpm. The pelleted nuclei were resuspended in four times the packed cell volume of nuclear extraction buffer (50 mM Tris, pH 7.5, 0.42 mM KCl, 6 mM DTT, 0.1 mM EDTA, 10% sucrose, 5 mM $MgCl_2$ 20% glycerol, 0.5 mM PMSF, 3 mg leupeptin per ml). The nuclei were then lysed by gentle rocking at 4° C. for 30 min at 4° C. Cytoplasmic and nuclear fractions were run on 15% SDS-PAGE followed by Western blot with anti-eIF4E antibody using ECL system with X-ray film. Densitometry of eIF4E bands was performed using GelDoc 2000 (purchased from BioRad) with Quantity One software.

Cell transduction with VPg protein. Transpass P (Ozyme) was combined with the purified VPg (0.1-2 μg/well) in 20 mM sodium phosphate, pH 7.0, containing 150 mM NaCl or in PBS according to the manufacturer instructions. Serum-free medium was added to the VPg/Transpass P mixture up to 250 μl final volume. HeLa cells ($10^5$/well of 24-well dish) prewashed with serum-free medium were treated with such portion of delivery mixture. After indicated periods of incubation at 37° C. cells were used for studies on protein localization (confocal microscopy) and on proliferation (LDH Kit from Clontech).

Localization of elE4E and VPg in insect cells by confocal microscopy. High Five (*T. ni*) cells in suspension ($2\times10^5$ cells/ml) were infected with 10 MOI of baculoviruses expressing either hisVPg, or his-tagged domain II of HCV helicase or empty bacmid. Cells were collected at 48 h p.i by centrifugation at 3000 rpm, 5 min, 4° C., followed by two washes with 500 μl of PBS. Cells were fixed in cold 2% PFA, left for 10 min at RT, washed two times with 500 μl of PBS and resuspended in 300 μl of PBS. Portions of 100 μl of fixed cells were applied onto clean round coverslips and allowed to attach while drying in a lamina flow hood. Next day cover slips were put into wells of 24-wells plate and rehydrated at room temperature with 500 μl portions of PBS. After PBS removal, cells were permeabilized for 10 min with cold 0.1% Triton X-100 in PBS, rinsed twice with PBS and blocked with 5% serum in PBS for 30 min at RT. Alter 2 washes with PBS cells were incubated for 1 h at RT with primary antibodies (anti-his or anti-human eIF4E) diluted 1/100 in PBS, followed by washing and 1 h incubation with secondary antibody (anti-rabbit FITC or anti-mouse Texas Red) (Jackson ImmunoResearch Laboratories) diluted 1:100 in PBS. Nuclei were stained with propidium iodide diluted in PBS (0.2-1 μg/ml). Alter three PBS rinses cover slips were mounted with 50% glycerol. Images were collected with BioRad MRC-600/Nikon Optiphot laser scanning confocal microscope.

Localization of eIF4E, VPg protein and PML in human cells by confocal microscopy. HeLa cells seeded on cover slips at about 60% confluency were washed 3 times with PBS and fixed in 2% cold PFA. Cells were infected with 10 MOI of baculoviruses expressing either hisVPg, or his-tagged domain 2 of HCV helicase or empty bacmid. Cells were collected at 48 h p.i by centrifugation at 3000 rpm, 5 min, 4° C., followed by two washes with 500 μl of PBS. Cells were fixed in cold 2% PFA, left for 10 min at Room Temperature, washed two times with 500 μl of PBS and resuspended in 300 μl of PBS. Portions of 100 μl of fixed cells were applied onto clean round coverslips and allowed to attach while drying in a lamina flow hood. Next day cover slips were put into wells of 24-wells plate and rehydrated min at room temperature with 500 μl portions of PBS. After PBS removal, cells were permeabilized for 10 min with cold 0.1% Triton X-100 in PBS, rinsed twice with PBS and blocked with 5% serum in PBS for 30 min at RT. After 2 washes with PBS cells were incubated for 1 h at room-temperature with primary antibodies (purified polyclonal anti-VPg, anti-eIF4E (MAb) and anti-PML (MAb) antibodies) diluted 1/100 in PBS, followed by washing and 1 h incubation with secondary antibody (anti-rabbit FITC or anti-mouse Texas Red) (purchased from Jackson ImmunoResearch Laboratories) diluted 1:100 in PBS. Nuclei were stained with propidium iodide diluted in PBS (0.2-1 μg/ml). After three PBS rinses cover slips were mounted with 50% glycerol. Images were collected with Bio-Rad MRC-600/Nikon Optiphot laser scanning confocal microscope.

Effect of VPg protein on cell proliferation.

HeLa, B16, GL26 and IMR90 cells were seeded in 96-wells plate at $1\times10^4$ cells per well and cultivated overnight. Portion of VPg (0.5-2 μg/well) was diluted into serum-free medium to obtain total volume 10 μl and incubated for 20 min with 0.2 μl TransPass P Protein Transfection Reagent (New England BioLabs) at room temperature. Cells were rinsed with serum-free medium and covered with 100 μl/well of mixture containing serum-free medium and transduction mix. After various time of incubation at 37° C. time the plates were centrifuged at 1000 rpm for 10 min and the supernatants were transferred to the new plate. The release of the malate dehydrogenase was measured with the LDH Cytotoxicity Detection Kit (Clontech), using multilabeled counter Victorl 412 (Wallac) at 490 nm. The level of cytotoxicity was calculated according to the LDH kit manual.

Example 2

In Vitro Interaction Assay of Human eIF4E with PVY VPg Protein and Fragments Thereof Peptides SEQ ID NO: 2 (VPg), SEQ ID NO: 14 (VPg2), SEQ ID NO: 16 (VPg4), SEQ ID NO: 20 (VPg1), SEQ ID NO: 22 (VPg3) and SEQ ID NO: 18 (VPg5) were obtained by expression in *E. coli* as GST-fusion proteins. GST-fusion proteins were produced by standard methods from cDNA sequences (encoding VPg, VPg1, VPg2, VPg3, VPg4 or VPg5) cloned into vector pGEX-4T-1 (purchased from Amersham Biosciences).

ELISA technique was used for measuring the peptide's interaction with eIF4E immobilised in wells of 96-well dish. The interaction was monitored with an anti-GST antibody.

Human eIF4E, 100 ng in the coating buffer (0.1 M carbonate buffer, pH 9.6) was applied to 96-wells micro titer plate for overnight at 4° C. Excess eIF4E was removed and the wells were blocked with 5% milk in the PBST buffer for 1 h at 37° C. The plate was rinsed three times with PBST and incubated with increasing quantity of the various GST-fusions peptides in PBST, for 1 h at RT. After two PBST washes the incubation with anti-GST HRP-conjugated antibody (1:5000) (purchased from Amersham Biosciences) was carried out for 30 min at 37° C. After three PBST washes the reaction was developed with peroxides substrate and the absorbance was measured at 490 nm. Non-specific interactions of GST protein and anti-GST antibody with the GST-fusion peptides were substracted.

Results are shown in FIG. 1. Among the peptides tested, it appeared that SEQ ID NO: 22 (VPg3) is the weaker interactor. SEQ ID NO: 20 (VPg1) and SEQ ID NO: 14 (VPg2) showed approximately similar level of interaction, which is not far from VPg itself. The best eIF4E-interacting peptide seems to be SEQ ID NO: 16 (VPg4) and SEQ ID NO: 18 (VPg5), which, at higher concentration functions better than PVY VPg protein itself (SEQ ID NO: 2).

Example 3

Figure 2:
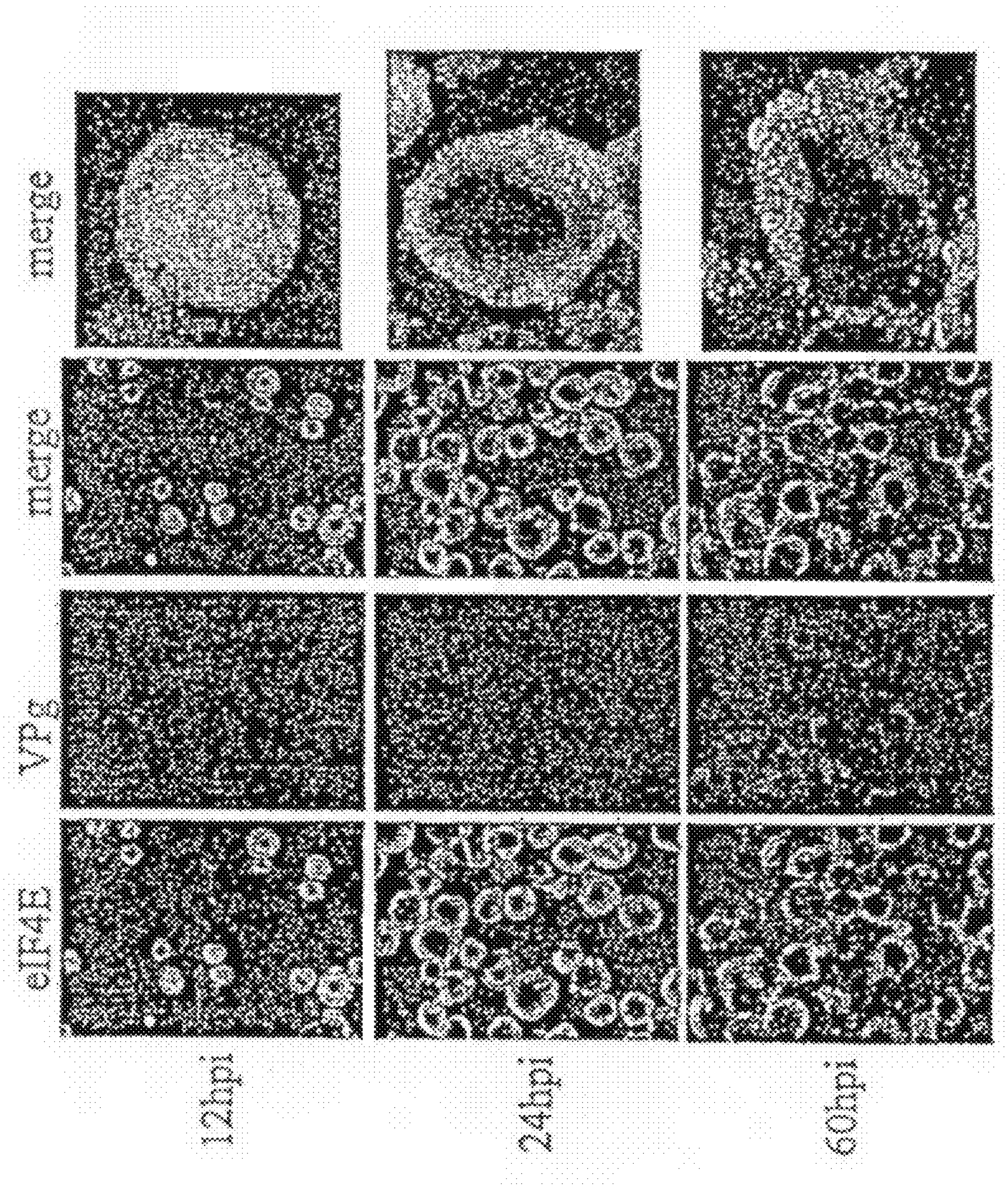
FIG. 2: Effect of VPg protein (SEQ ID NO: 2) expression on localization of native elF4E in insect cells. VPg was expressed in insect cells and distribution of native elF4E (left column) and recombinant VPg (VP column) was analyzed by confocal microscopy at the indicated timepoints post infection. The blow-ups of some cells are shown in the right column.

In Vitro Cellular Localisation of eIF4E and PVY VPg Protein (SEQ ID NO: 2) in Insect Cells Insect cells have been infected with baculovirus containing VPg gene of PVY (SEQ ID NO: 1). Confocal microscopy analysis revealed that the initiation factor eIF4E which localized at the beginning of infection in both compartiments, the nucleus and the cytoplasm (FIG. 2, 12 hpi), at 60 hpi timepoint was observed at the cell periphery (FIG. 2, left columns). VPg was observed only in the cytoplasm throughthout the infection (FIG. 2, VPg column). Merged images showed significant fraction of the eIF4E in the nucleus at the beginning of infection but which diminished in the course of infection; at 24 hpi, the eIF4E was visible in the cytoplasm and just at the nucleus periphery and at 60 hpi was observed in the cytoplasm only, showing significant overlap with the VPg.

Figure 3:
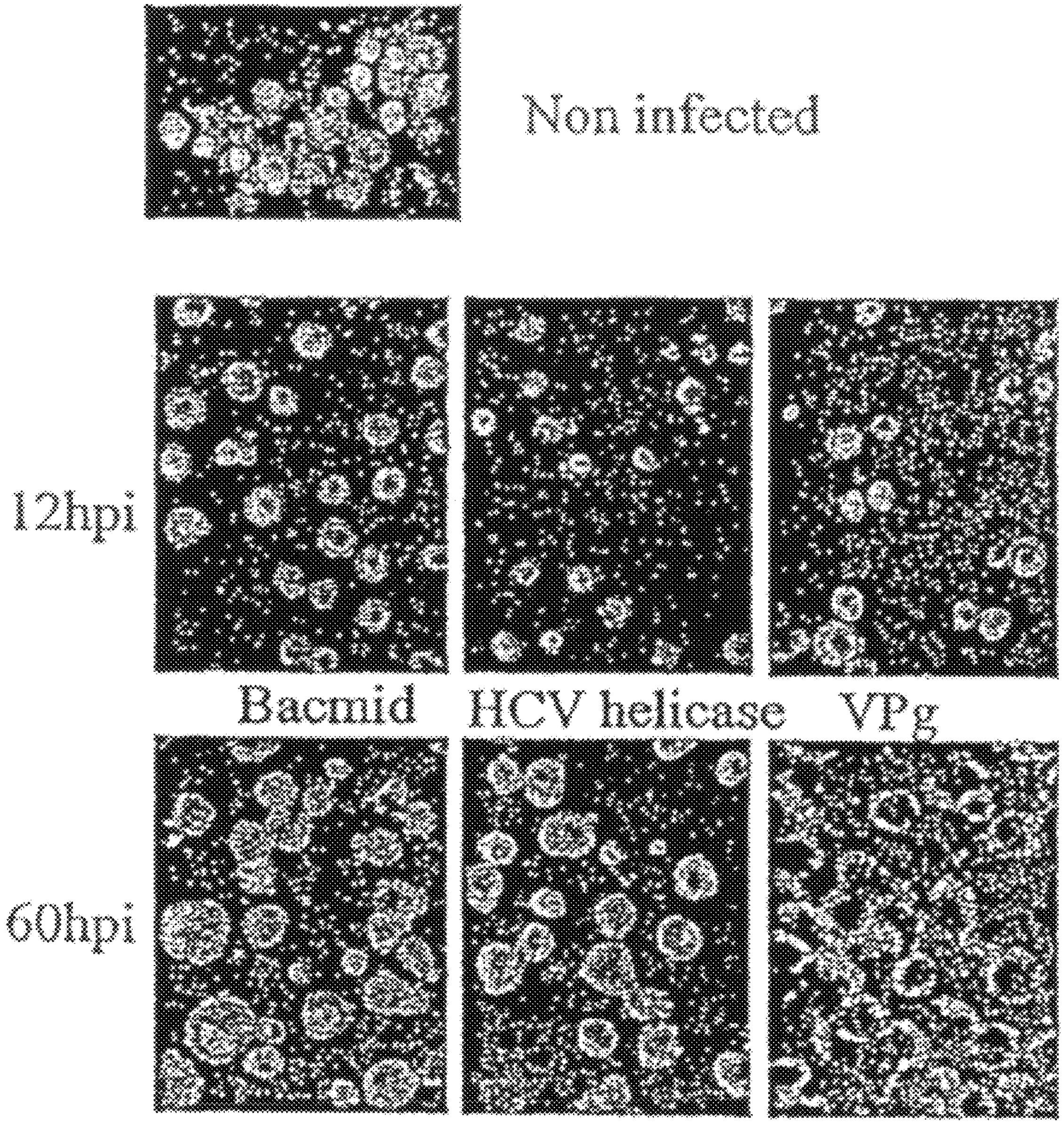
FIG. 3: Cytoplasmic retention of native elF4E is specific to VPg protein (SEQ ID NO: 2). Insect cells have been infected with bacmid (null baculovirus, left column), domain II of HCV helicase (middle column) and VPg (right column). Insect cells were analyzed by confocal microscopy at the indicated timepoints post infection.
Figure 4:
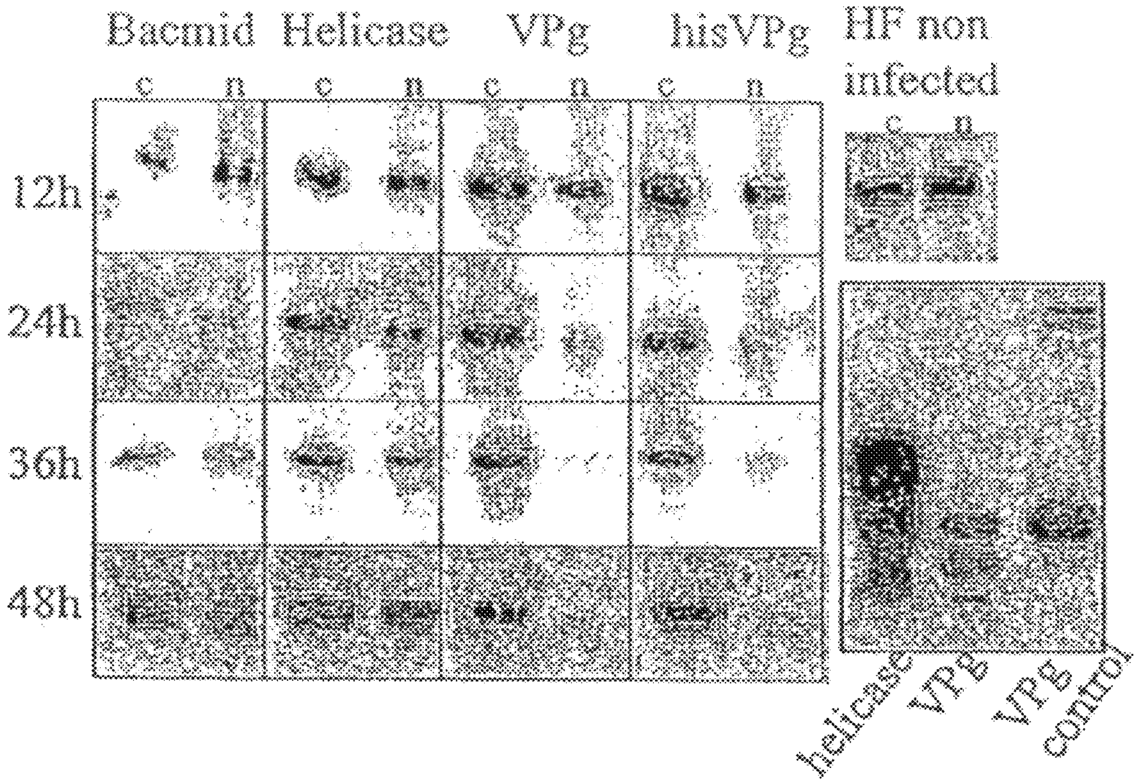
FIG. 4: elF4E expression in fractionated insect cells. Insect cells infected at MOI 10 with appropriate baculoviruses were collected at indicated timepoints post infection, nuclei were separated from the cytoplasm and the subcellular extracts were analysed by SDS/PAGE and Western blot. The expression of the recombinant proteins is shown on the far right lower panel.

To find out if the observed fluctuations in the eIF4E localization are specifically due to the presence of VPg, it was investigated the localization of eIF4E upon insect cells infection by baculovirus null (bacmid) which is a virus of origin, before insertion of the foreign gene, and also upon infection with baculovirus expressing non-relevant protein, the domain II of HCV helicase or VPg (FIG. 3). In non-infected insect cells eIF4E was observed in both cellular compartments (the most upper panel). At 12 hpi cells infected with all three kinds of virus behaved similarly, whereas al 60 hpi only cells expressing VPg showed eIF4E retention in the cytoplasm (FIG. 3, lowest panel). To obtain more quantitative data, the cell nucleus was separated from the cytoplasm, and eIF4E quantity in both compartiments was assessed by Western blot (FIG. 4) followed by densitometry (Table 2 below).

TABLE 2 eIF4E distribution in insect cell cytoplasm and nucleus

| Hours p.i. | baculovirus | eIF4E in cytoplasm (%) | eIF4E in nucleus (%) |
|---|---|---|---|
| HF cells | none | 48.49 | 51.51 |
| 12 h | bacmid | 46.5 | 53.5 |
| | HCV helicase domain | 51.54 | 48.46 |
| | VPg | 55.5 | 44.5 |
| | hisVPg | 53.45 | 46.55 |
| 24 h | bacmid | 57.83 | 42.17 |
| | HCV helicase domain | 63.05 | 36.95 |
| | VPg | 84.74 | 15.26 |
| | hisVPg | 81.3 | 18.7 |
| 36 h | bacmid | 59.2 | 40.8 |
| | HCV helicase domain | 62.5 | 37.5 |
| | VPg | 87.1 | 12.9 |
| | hisVPg | 83.33 | 16.67 |
| 48 h | bacmid | 55.99 | 44.01 |
| | HCV helicase domain | 57.9 | 42.1 |
| | VPg | 73.9 | 26.1 |
| | hisVPg | 74.07 | 25.93 |

Cells infected with the baculovirus expressing his-tagged form of VPg were included in the experiment. In both non infected as well as cells infected for 12 h, comparable level of eIF4E were present in the cytoplasm and the nucleus. The nuclear pool of the initiation factor diminished somewhat in the course of infection with bacmid and with helicase-expressing virus. However, upon expression of both VPg forms the nuclear pool of the eIF4E was severely depleted; at 36 hpi the nuclear pool of eIF4E accounted for 13% only of total cellular factor (down from 51-53%).

These experiments demonstrated that (1) VPg expressed alone in the baculovirus system remains in the cytoplasm; (2) in the presence of VPg, eIF4E is retained in the cytoplasm, resulting in the depletion of the initiation factor nuclear pool, but no inhibition of cell proliferation or cell death was observed probably because the insects cells contains several eIF4E isoforms.

Example 4

In Vitro Cellular Localization of eIF4E and PVY VPg Protein in Hela Cells

Figure 5:
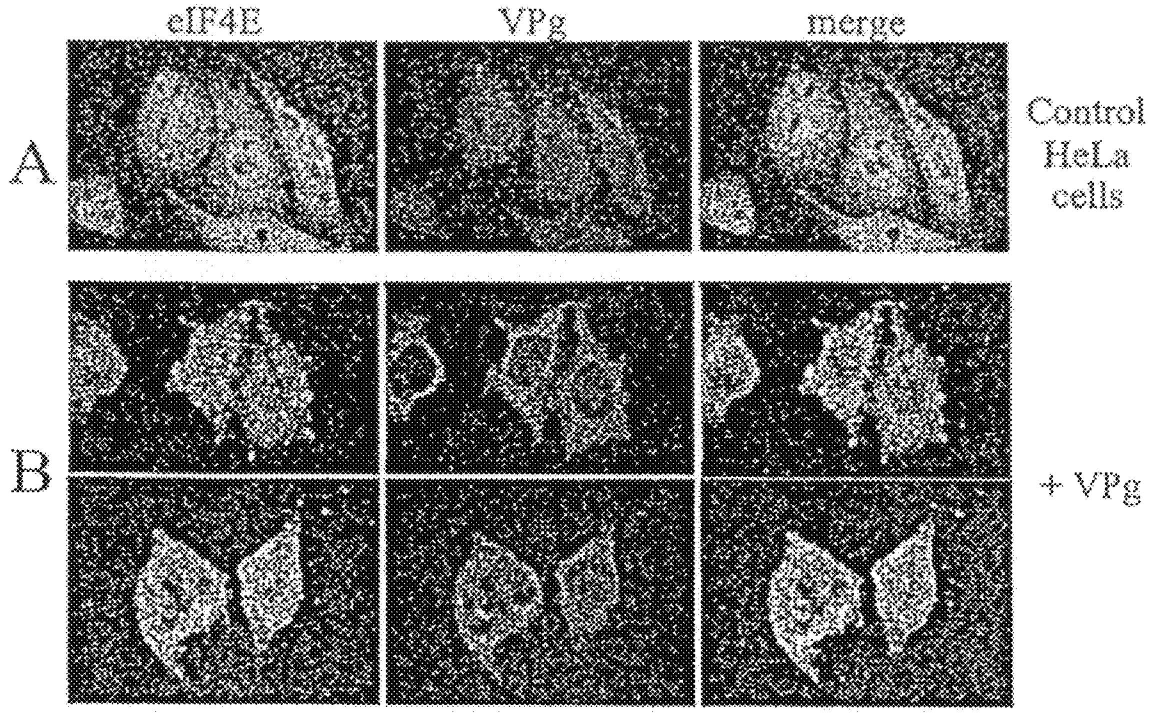
FIG. 5: Effect of PVY VPg protein on human eIF4E localisation. HeLa cells were transduced with VPg in the presence of Pro-Ject™ (purchased from Pierce) and analysed for presence of VPg and eIF4E by confocal miscroscopy (FIG. 1B).

In order to know if VPg protein of plant virus is able to interact with human eIF4E, and resulting in the depletion of the nuclear pool of the initiation factor, several tranfection experiments were undertaken under various conditions. However, no cells expressing VPg could be recovered, suggesting toxic effect of VPg on human cells. Therefore the PVY VPg (SEQ ID NO: 2) was directly translocated into HeLa cell with Pro-Ject™ (purchased from Pierce), a cationic lipid mixture which allows intracellular delivery of proteins (see FIG. 5B). VPg was localized in the cytoplasm and affected strongly localization of native eIF4E. The initiation factor in control HeLa cells was observed in cytoplasm and nucleus. In the presence of VPg the level of eIF4E diminished significantly in the nucleus and overlapped to large extent with the cytoplasm-localized VPg.

Example 5

Effect of PVY VPg Protein on Cell Proliferation In Vitro

Figure 6:
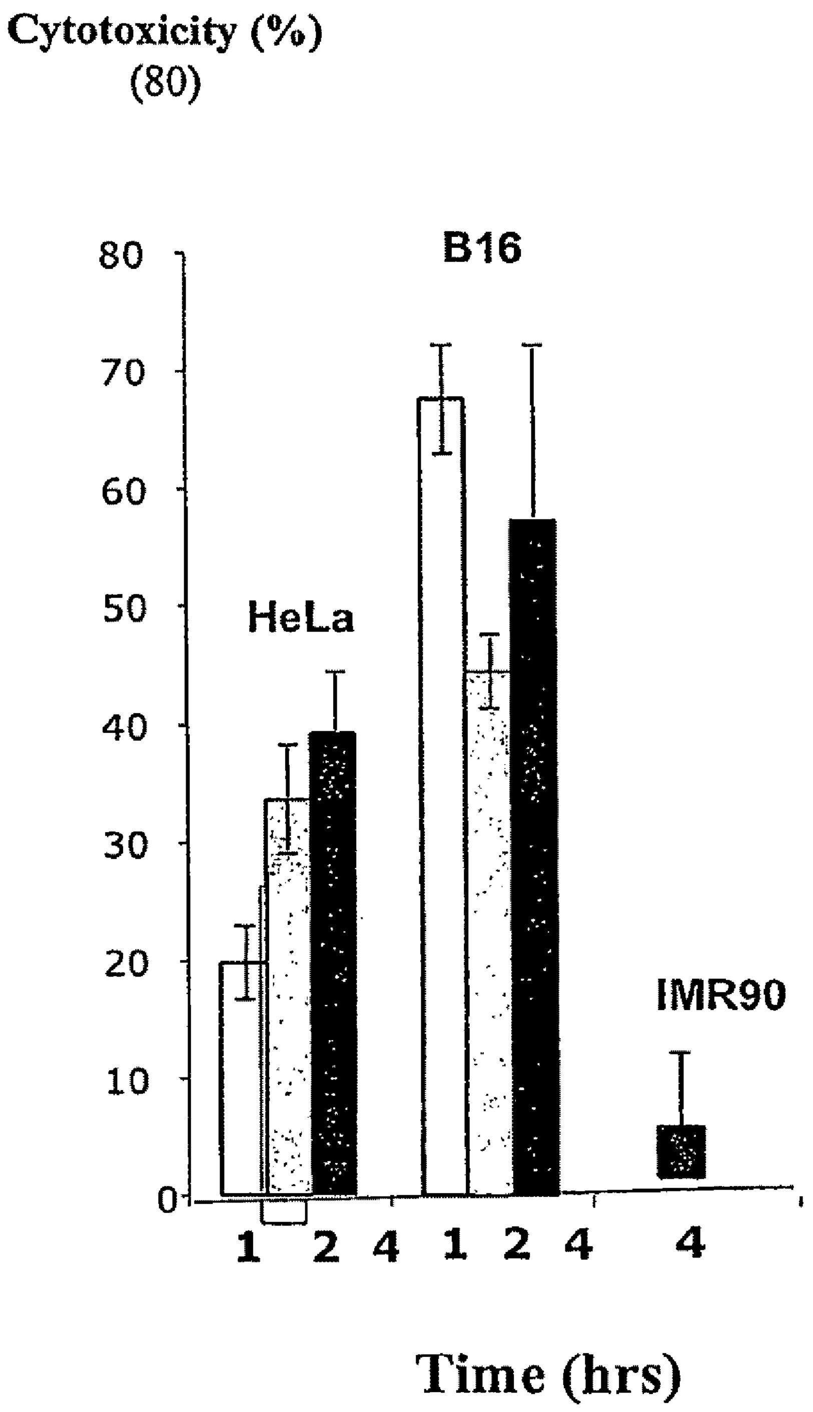
FIG. 6: Effect of PVY VPg protein on human cell proliferation. Cells were transduced with VPg using as protein transfer reagent TransPass P (Ozyme), and incubated for indicated periods. Cells damage was estimated using LDH Cytotoxicity detection assay (Clontech). The results show the average result obtained from three wells.

The LDH assay, which permits evaluation of cell damage was applied after VPg delivery to transformed cells, HeLa and B16 and to primary non-transformed human cells IMR90. Already 1 hour after VPg intracellular delivery both HeLa and B16 showed significant cell damage, Importantly, VPg introduced into primary IMR90 (human fetal lung fibroblasts) did not affect their growth (FIG. 6, IMR90).

The interaction of VPg with the eukaryotic initiation factor eIF4E results in the immobilization of the initation factor in the cytoplasm which leads to inhibition of cell growth followed by cell death. It is conceivable that the decrease of the eIF4E nuclear pool caused by interaction with VPg is accompanied by inhibition of the cytoplasmic transport of the messenger RNA of the pro-proliferative proteins, leading to the inhibition of cell growth with ensuing cell death.

Example 6

Efficacy of PVY VPg Protein on Cell Proliferation In Vivo

To study anticancer effect of PVY VPg protein (SEQ ID NO: 2), in vivo experiences have been undertaken. C57BL/6 mice were inoculated with GL26 cells inducing the mouse glioma tumours or with B16-ova melanoma cells.

GL26 tumours were established by injecting portions of $0.5\times10^6$ GL26 cells in 100 μl foetal bovine serum into the right quadriceps of the adult female C57BL/6 mice. About two weeks later, during the exponential phase of glioma tumour growth, the VPg (25 μg in 0.9% NaCl) or 0.9% NaCl (50 μl) (buffer) were administered by electroporation to 2 groups of 5 mice, leaving the control group of mice untreated. VPg and buffer treated mice were anaesthetized by intraperitoneal injection of 250 μl of a solution containing 400 μl of Imalgen 1000, 2% Rompun (both from Centravet, Lapalisse, France) and 0.9% NaCl. Electroporation conditions were the following: 5×100 μsec pulses of the 800 volts from electro square porator T820 (BTX, San Diego, Calif., U.S.A), at 1 Hz frequency. The delay between pulses was one second. The animals were kept warm (37° C.) until they recovered from anaesthesia. The volume of the tumours was measured in $mm^3$ every 2 or 3 days by slide calliper and compared with normally growing glioma tumors of the control untreated group of mice.

B16-ova melanoma tumours were established by injection of $5\times10^5$ cells suspended in PBS into the left thighs of the C57BL/6 mice (two groups of 8 animals). After 12 days, when palpable tumors were formed, the tumours of the control group were injected with Transpass P mixed with the buffer. Second group had the injections of 50 micrograms of VPg transduced with Transpass P, every day for 6 days. The kinetics of tumour growth was followed by measuring every day the tumor diameter.

Figure 7:
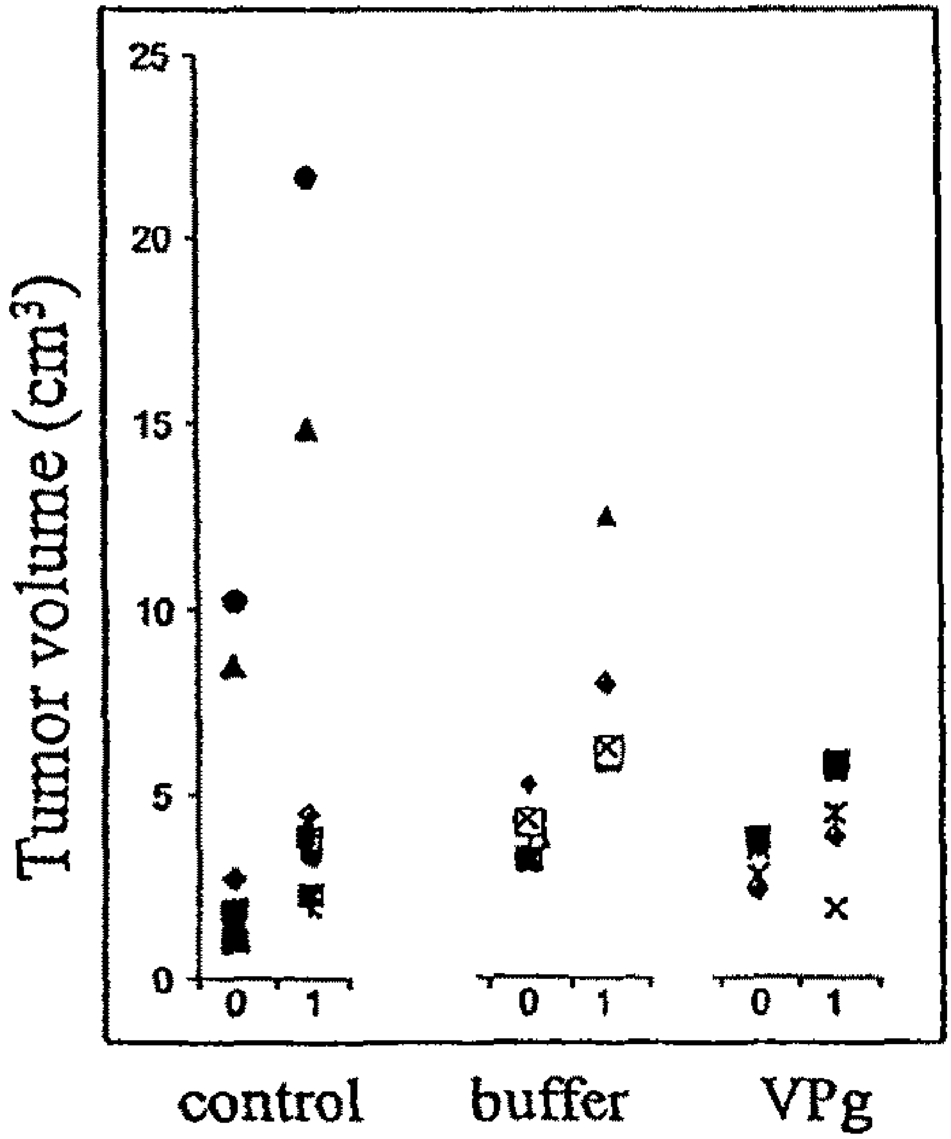
FIG. 7: Antitumour efficacy of PVY VPg protein in mice carrying GL26 (mouse glioma) tumours. 0=tumour volume measured at the beginning of the experiments. no treatment, 1=tumour volume measured 3 days later. Control=untreated mice. Buffer=mice electroporated with 0.9% NaCl. VPg=mice electroporated with 25 μg VPg in 0.9% NaCl. The same sign at the day 0 and 3 days later shows the volume of the tumour in the same mouse. The figure also give the fold increase in tumour size between time 0 and time 1 (fold 1 means no increase in tumour size).
Figure 8:
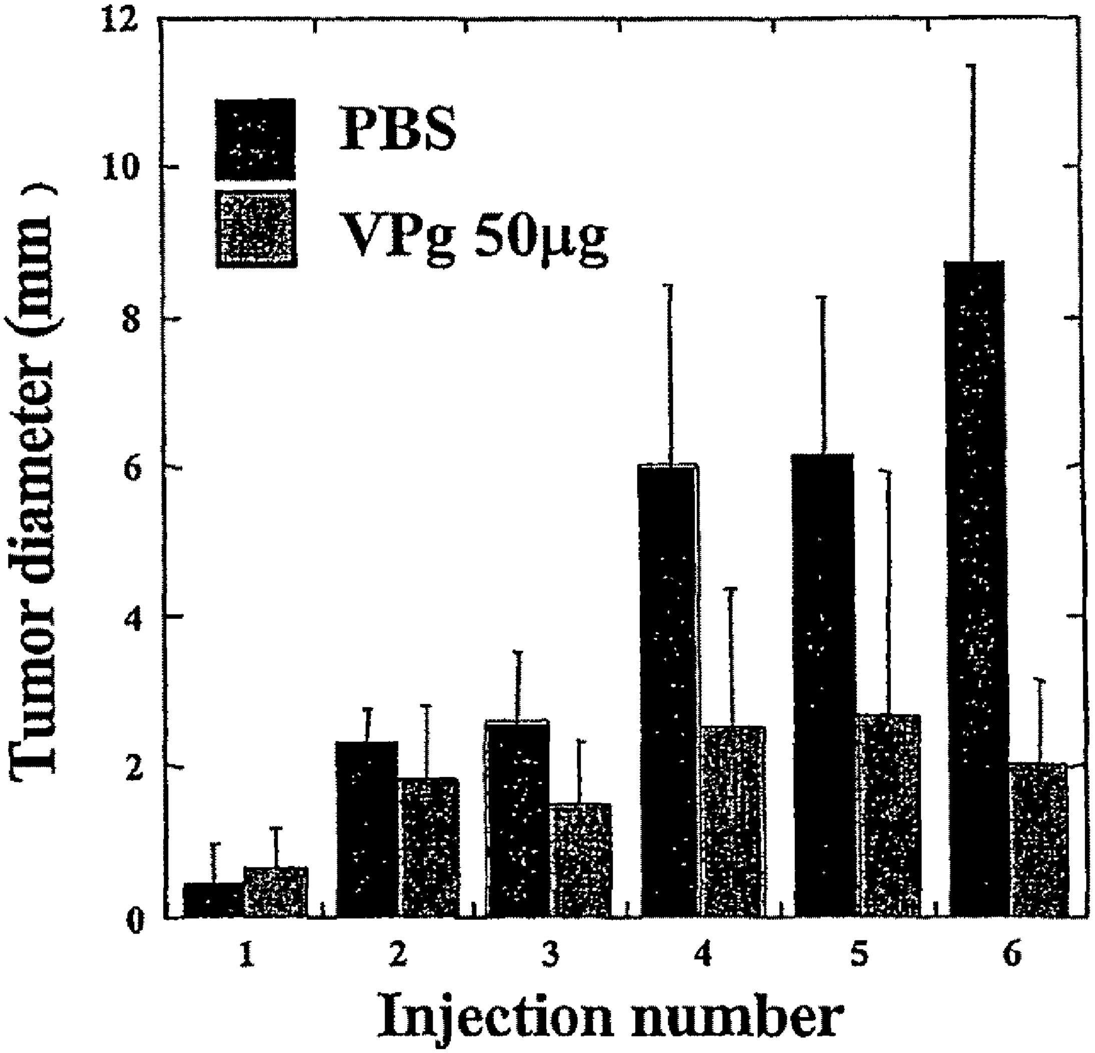
FIG. 8: Antitumour efficacy of PVY VPg protein in mice carrying B16-ova (murine melanoma) tumours. B16-ova melanoma cells were injected into the thigh of the C57BL/6 mice (two groups of 8 animals). Two weeks later palpable tumors were formed. Control group was injected into the tumor with buffer mixed with Transpass P. Second group had injections of 50 micrograms of VPg transduced with Transpass P. every day for 6 days. The diameter of the tumours were measured every day during six days of treatment.

Results are shown in FIGS. 7 and 8. Administration of VPg slowed down or inhibited the growth of the tumours in comparison with control groups. This shows that VPg has indeed an inhibitory effect on tumour proliferation.

REFERENCES

Boguszewska-Chachulska A M, Krawczyk M, Stankiewicz A, Gozdek A, Haenni A L, Strokovskaya L. (2004) Direct fluorometric measurement of hepatitis C virus helicase activity. *FEBS Lett.* 567:253-6.

Chaudhry Y, Nayak A, Bordeleau M E, Tanaka J, Pelletier J, Belsham G J, Roberts L O, Goodfellow I G. (2006) Caliciviruses differ in their functional requirements for eIF4F components. *J. Biol. Chem.* 281:25315-25.

Derossi D, Calvet S, Trembleau A, Brunissen A, Chassaing G, Prochiantz A. (1996) Cell internalization of the third helix of the Antennapedia homeodomain is receptor-independent. *J. Biol. Chem.* 271:18188-93.

Duprat A, Caranta C, Revers F, Menand B, Browning K S, Robaglia C. (2002) The *Arabidopsis* eukaryotic initiation factor (iso)4E is dispensable for plant growth but required for susceptibility to potyviruses. *Plant J.* 32:927-34.

Elliott G and O'Hare P. (1997) Intercellular trafficking and protein delivery by a herpesvirus structural protein. *Cell* 88:223-33.

Fellers, J, Wan J, Hong Y, Collins G B, and Hunt A G. (1998). In vitro interactions between a potyvirus-encoded, genome-linked protein and RNA-dependent RNA polymerase. *J. Gen. Virol.* 79:2043-2049.

Goodfellow I, Chaudhry Y, Gioldasi I, Gerondopoulos A, Natoni A, Labrie L, Laliberte J F, Roberts L. (2005) Calicivirus translation initiation requires an interaction between VPg and eIF4E. *EMBO Rep.* 6: 968-972.

Grzela R, Strokovska L, Andrieu J P, Dublet B, Zagorski W, Chroboczek J. (2006) Potyvirus terminal protein VPg, effector of host eukaryotic initiation factor eIF4E *Biochimie* 88:887-96.

Herbert T P, Brierley I, Brown T D. (1997) Identification of a protein linked to the genomic and subgenomic mRNAs of feline calicivirus and its role in translation. *J. Gen Virol.* 78:1033-40.

Jans D A. (1994) Nuclear signaling pathways for peptide ligands and their membrane receptors? *Faseb J.* 8:841-847

Kang B C, Yearn I, Frantz J D, Murphy J F, Jahn M M. (2005) The pvr1 locus in *Capsicum* encodes a translation initiation factor eIF4E that interacts with Tobacco etch virus VPg. *Plant J.* 42:392-405.

Kokryakov V N, Harwig S S, Panyutich E A, Shevchenko A A, Aleshina G M, Shamova O V, Korneva H A, Lehrer R1. (1993) Protegrins: leukocyte antimicrobial peptides that combine features of corticostatic defensins and tachyplesins. *FEBS Lett.* 327:231-6.

Lai H K, Borden K L, (2000) The promyelocytic leukemia (PML) protein suppresses cyclin D1 protein production by altering the nuclear cytoplasmic distribution of cyclin D1 mRNA. *Oncogene* 19:1623-34.

Lejbkowicz F, Goyer C, Darveau A, Neron S, Lemieux R, Sonenberg N. (1992) A fraction of the mRNA 5' cap-binding protein, eukaryotic initiation factor 4E, localizes to the nucleus. *Proc Natl Acad Sci USA.* 89:9612-6.

Lellis A D, Kasschau K D, Whitham S A, Carrington J C. (2002) Loss-of-susceptibility mutants of *Arabidopsis thaliana* reveal an essential role for eIF(iso)$_4$E during potyvirus infection. *Curr Biol.* 12:1046-51

Leonard S, Plante D, Wittmann S, Daigneault N, Fortin M G, Laliberte J F. (2000) Complex formation between potyvirus VPg and translation eukaryotic initiation factor 4E correlates with virus infectivity. *J. Virol.* 74:7730-7.

Murphy J F, Rychlik W, Rhoads R E, Hunt A G, Shaw J G. (1991) A tyrosine residue in the small nuclear inclusion protein of tobacco vein mottling virus links the VPg to the viral RNA. *J. Virol.* 65:511-3.

O'Reilly D R, Miller L K and Luckow V A. (1992) Baculovirus Expression Vectors: A Laboratory Manual. (New York, N.Y.: W.H. Freemean and Company).

Riechmann J L, Lain S, Garcia J A. (1989) The genome-linked protein and 5' end RNA sequence of plum pox potyvirus. *J Gen Virol.* 70:2785-9.

Rosenwald I B, Kaspar R, Rousseau D, Gehrke L, Leboulch P, Chen J J, Schmidt E V, Sonenberg N, London I M. (1995) Eukaryotic translation initiation factor 4E regulates expression of cyclin D1 at transcriptional and post-transcriptional levels. *J Biol Chem.* 270:21176-80.

Rousseau D, Kaspar R, Rosenwald I, Gehrke L, Sonenberg N. (1996) Translation initiation of ornithine decarboxylase and nucleocytoplasmic transport of cyclin D1 mRNA are increased in cells overexpressing eukaryotic initiation factor 4E. *Proc Natl Acad Sci USA.* 93:1065-70.

Ruben S, Perkins A, Purcell R, Joung K, Sia R, Burghoff R, Haseltine W A, Rosen C A. (1989) Structural and functional characterization of human immunodeficiency virus tat protein. *J. Virol.* 63:1-8.

Ruggero D and Pandolfi P P. (2003) Does the ribosome translate cancer? *Nat. Rev. Cancer.* 3:179-92.

Schaad M C, Lellis A D, and Carrington J C. (1997) VPg of tobacco etch potyvirus is a host genotype-specific determinant for long-distance movement. *J. Virol.* 71:8624-8631.

Shantz L M, Pegg A E. (1994) Overproduction of ornithine decarboxylase caused by relief of translational repression s associated with neoplastic transformation. *Cancer Res.* 54:2313-6.

Sonenberg N, Gingras A C. (1998) The mRNA 5' cap-binding protein eIF4E and control of cell growth. *Curr Opin Cell Biol.* 10:268-75.

Wittmann S, Chatel H, Fortin M G, Laliberte J F. (1997) Interaction of the viral protein genome linked of turnip mosaic potyvirus with the translational eukaryotic initiation factor (iso) 4E of *Arabidopsis thaliana* using the yeast two-hybrid system. *Virology.* 234:84-92.

The invention claimed is:

1. A method of treating cancer in which the initiation factor eIF4E is expressed, in a subject in need thereof, comprising administering to said subject a therapeutically effective amount of a composition comprising an isolated and purified protein comprising or consisting of a VPg protein or fragment thereof having the ability to bind an eukaryotic intiation factor eIF4E, wherein the VPg protein or fragment thereof is selected from the group consisting of SEQ ID NO: 2, SEQ ID NO: 14, SEQ ID NO: 16, SEQ ID NO: 18, and SEQ ID NO: 20.

2. The method according to claim 1, wherein the VPg protein or fragment thereof has the ability to bind a mammalian initiation factor eIF4E.

3. The method according to claim 1, wherein the VPg protein or fragment thereof has the ability to bind a human initiation factor eIF4E.

4. The method according to claim 1, wherein said composition comprises a purified protein comprising or consisting of the VPg protein of SEQ ID NO: 2.

5. The method according to claim 1, wherein said composition comprises a purified protein comprising or consisting of the VPg protein fragment of SEQ ID NO: 14.

6. The method according to claim 1, wherein said composition comprises a purified protein comprising or consisting of the VPg protein fragment of SEQ ID NO: 16.

7. The method according to claim 1, wherein said composition comprises a purified protein comprising or consisting of the VPg protein fragment of SEQ ID NO: 18.

8. The method according to claim 1, wherein said composition comprises a purified protein comprising or consisting of the VPg protein fragment of SEQ ID NO: 20.

9. The method according to claim 1, wherein said cancer is a glioma, melanoma or a colon or lung cancer, in which the cancer cells express the initiation factor eIF4E.

10. The method according to claim 1, wherein said cancer is a lung cancer.

* * * * *

UNITED STATES PATENT AND TRADEMARK OFFICE

CERTIFICATE OF CORRECTION

PATENT NO. : 8,324,150 B2
APPLICATION NO. : 12/664240
DATED : December 4, 2012
INVENTOR(S) : Jadwiga Chroboczek et al.

It is certified that error appears in the above-identified patent and that said Letters Patent is hereby corrected as shown below:

In Claim 1, at Column 43, line 26, delete "intiation" and replace it with -- initiation --.

Signed and Sealed this
Twelfth Day of March, 2013

Teresa Stanek Rea
*Acting Director of the United States Patent and Trademark Office*

UNITED STATES PATENT AND TRADEMARK OFFICE

CERTIFICATE OF CORRECTION

PATENT NO. : 8,324,150 B2
APPLICATION NO. : 12/664240
DATED : December 4, 2012
INVENTOR(S) : Chroboczek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Eleventh Day of June, 2013

Teresa Stanek Rea
*Acting Director of the United States Patent and Trademark Office*

SEQUENCE LISTING

```
<160> NUMBER OF SEQ ID NOS: 31

<210> SEQ ID NO 1
<211> LENGTH: 564
<212> TYPE: DNA
<213> ORGANISM: Potato virus Y
<220> FEATURE:
<221> NAME/KEY: CDS
<222> LOCATION: (1)..(564)

<400> SEQUENCE: 1

ggg aaa aat aaa tcc aag aga atc caa gcc ttg aag ttt cgc cat gct       48
Gly Lys Asn Lys Ser Lys Arg Ile Gln Ala Leu Lys Phe Arg His Ala
1               5                   10                  15

cgt gac aaa agg gct ggc ttt gaa att gac aac aat gat gac aca ata       96
Arg Asp Lys Arg Ala Gly Phe Glu Ile Asp Asn Asn Asp Asp Thr Ile
            20                  25                  30

gag gaa ttc ttt gga tct gca tac agg aaa aag gga aaa ggt aaa ggt      144
Glu Glu Phe Phe Gly Ser Ala Tyr Arg Lys Lys Gly Lys Gly Lys Gly
        35                  40                  45

acc aca gtt ggt atg ggc aag tca agc agg agg ttc att aac atg tac      192
Thr Thr Val Gly Met Gly Lys Ser Ser Arg Arg Phe Ile Asn Met Tyr
    50                  55                  60

ggg ttc gac cca aca gag tac tca ttc atc caa ttc gtt gat cca ctc      240
Gly Phe Asp Pro Thr Glu Tyr Ser Phe Ile Gln Phe Val Asp Pro Leu
65                  70                  75                  80

act ggg gca caa ata gaa gag aat gtc tat gct gac att aga gat att      288
Thr Gly Ala Gln Ile Glu Glu Asn Val Tyr Ala Asp Ile Arg Asp Ile
                85                  90                  95

caa gag aga ttt agt gaa gtg cga aag aaa atg gtt gag aat gat gac      336
Gln Glu Arg Phe Ser Glu Val Arg Lys Lys Met Val Glu Asn Asp Asp
            100                 105                 110
```

```
att gaa atg caa gcc ttg ggt agt aac acg acc ata cat gca tac ttt      384
Ile Glu Met Gln Ala Leu Gly Ser Asn Thr Thr Ile His Ala Tyr Phe
        115                 120                 125

agg aaa gat tgg tct gac aaa gct ttg aag att gat tta atg cca cat      432
Arg Lys Asp Trp Ser Asp Lys Ala Leu Lys Ile Asp Leu Met Pro His
    130                 135                 140

aac cca ctc aaa gtt tgt gac aaa aca aat ggc att gcc aaa ttt cct      480
Asn Pro Leu Lys Val Cys Asp Lys Thr Asn Gly Ile Ala Lys Phe Pro
145                 150                 155                 160

gag aga gag ctc gaa cta agg cag act ggg cca gct gta gaa gtc gac      528
Glu Arg Glu Leu Glu Leu Arg Gln Thr Gly Pro Ala Val Glu Val Asp
                165                 170                 175

gtg aag gac ata cca gcg cag gag gtg gag cat gaa                      564
Val Lys Asp Ile Pro Ala Gln Glu Val Glu His Glu
            180                 185


<210> SEQ ID NO 2
<211> LENGTH: 188
<212> TYPE: PRT
<213> ORGANISM: Potato virus Y

<400> SEQUENCE: 2

Gly Lys Asn Lys Ser Lys Arg Ile Gln Ala Leu Lys Phe Arg His Ala
1               5                   10                  15

Arg Asp Lys Arg Ala Gly Phe Glu Ile Asp Asn Asn Asp Asp Thr Ile
            20                  25                  30

Glu Glu Phe Phe Gly Ser Ala Tyr Arg Lys Lys Gly Lys Gly Lys Gly
        35                  40                  45

Thr Thr Val Gly Met Gly Lys Ser Ser Arg Arg Phe Ile Asn Met Tyr
    50                  55                  60

Gly Phe Asp Pro Thr Glu Tyr Ser Phe Ile Gln Phe Val Asp Pro Leu
65                  70                  75                  80

Thr Gly Ala Gln Ile Glu Glu Asn Val Tyr Ala Asp Ile Arg Asp Ile
                85                  90                  95

Gln Glu Arg Phe Ser Glu Val Arg Lys Lys Met Val Glu Asn Asp Asp
            100                 105                 110

Ile Glu Met Gln Ala Leu Gly Ser Asn Thr Thr Ile His Ala Tyr Phe
        115                 120                 125

Arg Lys Asp Trp Ser Asp Lys Ala Leu Lys Ile Asp Leu Met Pro His
    130                 135                 140

Asn Pro Leu Lys Val Cys Asp Lys Thr Asn Gly Ile Ala Lys Phe Pro
145                 150                 155                 160

Glu Arg Glu Leu Glu Leu Arg Gln Thr Gly Pro Ala Val Glu Val Asp
                165                 170                 175

Val Lys Asp Ile Pro Ala Gln Glu Val Glu His Glu
            180                 185


<210> SEQ ID NO 3
<211> LENGTH: 564
<212> TYPE: DNA
<213> ORGANISM: Tobacco etch virus
<220> FEATURE:
<221> NAME/KEY: CDS
<222> LOCATION: (1)..(564)

<400> SEQUENCE: 3

ggg aag aag aat cag aag cac aag ctt aag atg aga gag gcg cgt ggg       48
Gly Lys Lys Asn Gln Lys His Lys Leu Lys Met Arg Glu Ala Arg Gly
1               5                   10                  15
```

```
gct aga ggg caa tat gag gtt gca gcg gag cca gag gcg cta gaa cat         96
Ala Arg Gly Gln Tyr Glu Val Ala Ala Glu Pro Glu Ala Leu Glu His
            20                  25                  30

tac ttt gga agc gca tat aat aac aaa gga aag cgc aag ggc acc acg        144
Tyr Phe Gly Ser Ala Tyr Asn Asn Lys Gly Lys Arg Lys Gly Thr Thr
        35                  40                  45

aga gga atg ggt gca aag tct cgg aaa ttc ata aac atg tat ggg ttt        192
Arg Gly Met Gly Ala Lys Ser Arg Lys Phe Ile Asn Met Tyr Gly Phe
    50                  55                  60

gat cca act gat ttt tca tac att agg ttt gtg gat cca ttg aca ggt        240
Asp Pro Thr Asp Phe Ser Tyr Ile Arg Phe Val Asp Pro Leu Thr Gly
65                  70                  75                  80

cac act att gat gag tcc aca aac gca cct att gat tta gtg cag cat        288
His Thr Ile Asp Glu Ser Thr Asn Ala Pro Ile Asp Leu Val Gln His
                85                  90                  95

gag ttt gga aag gtt aga aca cgc atg tta att gac gat gag ata gag        336
Glu Phe Gly Lys Val Arg Thr Arg Met Leu Ile Asp Asp Glu Ile Glu
            100                 105                 110

cct caa agt ctt agc acc cac acc aca atc cat gct tat ttg gtg aat        384
Pro Gln Ser Leu Ser Thr His Thr Thr Ile His Ala Tyr Leu Val Asn
        115                 120                 125

agt ggc acg aag aaa gtt ctt aag gtt gat tta aca cca cac tcg tcg        432
Ser Gly Thr Lys Lys Val Leu Lys Val Asp Leu Thr Pro His Ser Ser
    130                 135                 140

cta cgt gcg agt gag aaa tca aca gca ata atg gga ttt cct gaa agg        480
Leu Arg Ala Ser Glu Lys Ser Thr Ala Ile Met Gly Phe Pro Glu Arg
145                 150                 155                 160

gag aat gaa ttg cgt caa acc ggc atg gca gtg cca gtg gct tat gat        528
Glu Asn Glu Leu Arg Gln Thr Gly Met Ala Val Pro Val Ala Tyr Asp
                165                 170                 175

caa ttg cca cca aag aat gag gac ttg acg ttt gaa                        564
Gln Leu Pro Pro Lys Asn Glu Asp Leu Thr Phe Glu
            180                 185


<210> SEQ ID NO 4
<211> LENGTH: 188
<212> TYPE: PRT
<213> ORGANISM: Tobacco etch virus

<400> SEQUENCE: 4

Gly Lys Lys Asn Gln Lys His Lys Leu Lys Met Arg Glu Ala Arg Gly
1               5                   10                  15

Ala Arg Gly Gln Tyr Glu Val Ala Ala Glu Pro Glu Ala Leu Glu His
            20                  25                  30

Tyr Phe Gly Ser Ala Tyr Asn Asn Lys Gly Lys Arg Lys Gly Thr Thr
        35                  40                  45

Arg Gly Met Gly Ala Lys Ser Arg Lys Phe Ile Asn Met Tyr Gly Phe
    50                  55                  60

Asp Pro Thr Asp Phe Ser Tyr Ile Arg Phe Val Asp Pro Leu Thr Gly
65                  70                  75                  80

His Thr Ile Asp Glu Ser Thr Asn Ala Pro Ile Asp Leu Val Gln His
                85                  90                  95

Glu Phe Gly Lys Val Arg Thr Arg Met Leu Ile Asp Asp Glu Ile Glu
            100                 105                 110

Pro Gln Ser Leu Ser Thr His Thr Thr Ile His Ala Tyr Leu Val Asn
        115                 120                 125

Ser Gly Thr Lys Lys Val Leu Lys Val Asp Leu Thr Pro His Ser Ser
    130                 135                 140

Leu Arg Ala Ser Glu Lys Ser Thr Ala Ile Met Gly Phe Pro Glu Arg
```

-continued

```
145                 150                 155                 160

Glu Asn Glu Leu Arg Gln Thr Gly Met Ala Val Pro Val Ala Tyr Asp
                165                 170                 175

Gln Leu Pro Pro Lys Asn Glu Asp Leu Thr Phe Glu
            180                 185


<210> SEQ ID NO 5
<211> LENGTH: 573
<212> TYPE: DNA
<213> ORGANISM: Clover yellow vein virus
<220> FEATURE:
<221> NAME/KEY: CDS
<222> LOCATION: (1)..(573)

<400> SEQUENCE: 5

ggg aaa agt aag aga aca aga caa aag ttg aag ttc aga gcg gca aga       48
Gly Lys Ser Lys Arg Thr Arg Gln Lys Leu Lys Phe Arg Ala Ala Arg
1               5                   10                  15

gac atg aag gat cgt tat gaa gtg cat gcc gat gag ggg act tta gtg       96
Asp Met Lys Asp Arg Tyr Glu Val His Ala Asp Glu Gly Thr Leu Val
            20                  25                  30

gaa aat ttt gga act cgt tat tca aag aaa ggc aag aca aaa ggt act      144
Glu Asn Phe Gly Thr Arg Tyr Ser Lys Lys Gly Lys Thr Lys Gly Thr
        35                  40                  45

gtt gtg ggt ttg ggt gca aaa aca aga cgg ttc act aac atg tat ggt      192
Val Val Gly Leu Gly Ala Lys Thr Arg Arg Phe Thr Asn Met Tyr Gly
    50                  55                  60

ttt gac ccc acg gag tat tca ttt gct agg tat ctt gat cca atc acg      240
Phe Asp Pro Thr Glu Tyr Ser Phe Ala Arg Tyr Leu Asp Pro Ile Thr
65                  70                  75                  80

ggt gca aca ttg gat gaa acc cca att cac aat gta aat ttg gtt gct      288
Gly Ala Thr Leu Asp Glu Thr Pro Ile His Asn Val Asn Leu Val Ala
                85                  90                  95

gag cat ttt ggc gac ata agg ctt gat atg gtt gac aag gag tta ctt      336
Glu His Phe Gly Asp Ile Arg Leu Asp Met Val Asp Lys Glu Leu Leu
            100                 105                 110

gac aaa cag cac tta tac ctc aag aga cca ata gaa tgt tac ttt gta      384
Asp Lys Gln His Leu Tyr Leu Lys Arg Pro Ile Glu Cys Tyr Phe Val
        115                 120                 125

aag gat gct ggt cag aag gtg atg agg att gat cta aca ccc cac aac      432
Lys Asp Ala Gly Gln Lys Val Met Arg Ile Asp Leu Thr Pro His Asn
    130                 135                 140

cca ttg ttg gca agc gat gtt agc aca acc ata atg ggt tat cct gag      480
Pro Leu Leu Ala Ser Asp Val Ser Thr Thr Ile Met Gly Tyr Pro Glu
145                 150                 155                 160

aga gaa ggt gaa ctc cgt caa act gga aag gca agg tta gtc gac cca      528
Arg Glu Gly Glu Leu Arg Gln Thr Gly Lys Ala Arg Leu Val Asp Pro
                165                 170                 175

tca gag ttg ccc gcg cgg aat gag gat att gat gca gag ttt gag          573
Ser Glu Leu Pro Ala Arg Asn Glu Asp Ile Asp Ala Glu Phe Glu
            180                 185                 190


<210> SEQ ID NO 6
<211> LENGTH: 191
<212> TYPE: PRT
<213> ORGANISM: Clover yellow vein virus

<400> SEQUENCE: 6

Gly Lys Ser Lys Arg Thr Arg Gln Lys Leu Lys Phe Arg Ala Ala Arg
1               5                   10                  15

Asp Met Lys Asp Arg Tyr Glu Val His Ala Asp Glu Gly Thr Leu Val
            20                  25                  30
```

-continued

```
Glu Asn Phe Gly Thr Arg Tyr Ser Lys Lys Gly Lys Thr Lys Gly Thr
        35                  40                  45

Val Val Gly Leu Gly Ala Lys Thr Arg Arg Phe Thr Asn Met Tyr Gly
    50                  55                  60

Phe Asp Pro Thr Glu Tyr Ser Phe Ala Arg Tyr Leu Asp Pro Ile Thr
65                  70                  75                  80

Gly Ala Thr Leu Asp Glu Thr Pro Ile His Asn Val Asn Leu Val Ala
                85                  90                  95

Glu His Phe Gly Asp Ile Arg Leu Asp Met Val Asp Lys Glu Leu Leu
            100                 105                 110

Asp Lys Gln His Leu Tyr Leu Lys Arg Pro Ile Glu Cys Tyr Phe Val
        115                 120                 125

Lys Asp Ala Gly Gln Lys Val Met Arg Ile Asp Leu Thr Pro His Asn
    130                 135                 140

Pro Leu Leu Ala Ser Asp Val Ser Thr Thr Ile Met Gly Tyr Pro Glu
145                 150                 155                 160

Arg Glu Gly Glu Leu Arg Gln Thr Gly Lys Ala Arg Leu Val Asp Pro
                165                 170                 175

Ser Glu Leu Pro Ala Arg Asn Glu Asp Ile Asp Ala Glu Phe Glu
            180                 185                 190


<210> SEQ ID NO 7
<211> LENGTH: 549
<212> TYPE: DNA
<213> ORGANISM: Tobacco vein mottling virus
<220> FEATURE:
<221> NAME/KEY: CDS
<222> LOCATION: (1)..(549)

<400> SEQUENCE: 7

ggc aag agt aga cgc cga ctt caa ttc aga aaa gca agg gac gat aag       48
Gly Lys Ser Arg Arg Arg Leu Gln Phe Arg Lys Ala Arg Asp Asp Lys
1               5                   10                  15

atg ggt tat atc atg cat ggt gaa ggg gac aca att gaa cat ttc ttt       96
Met Gly Tyr Ile Met His Gly Glu Gly Asp Thr Ile Glu His Phe Phe
            20                  25                  30

ggc gcg gcc tat aca aag aaa gga aag tcc aaa ggg aaa act cat ggc      144
Gly Ala Ala Tyr Thr Lys Lys Gly Lys Ser Lys Gly Lys Thr His Gly
        35                  40                  45

gct gga acg aag gcg cac aaa ttt gtg aat atg tat gga gtc agt cct      192
Ala Gly Thr Lys Ala His Lys Phe Val Asn Met Tyr Gly Val Ser Pro
    50                  55                  60

gat gaa tat tca tat gta cgt tat cta gat cca gtc acg ggt gcg act      240
Asp Glu Tyr Ser Tyr Val Arg Tyr Leu Asp Pro Val Thr Gly Ala Thr
65                  70                  75                  80

cta gat gaa tct cca atg aca gac tta aac att gtg caa gaa cac ttt      288
Leu Asp Glu Ser Pro Met Thr Asp Leu Asn Ile Val Gln Glu His Phe
                85                  90                  95

gga gaa atc agg agg gaa gct ata ctt gct gat gca atg tca cca caa      336
Gly Glu Ile Arg Arg Glu Ala Ile Leu Ala Asp Ala Met Ser Pro Gln
            100                 105                 110

caa agg aac aag gga atc cag gca tac ttt gtt aga aat tca aca atg      384
Gln Arg Asn Lys Gly Ile Gln Ala Tyr Phe Val Arg Asn Ser Thr Met
        115                 120                 125

cca att ctc aaa gtt gat ctg aca cca cac att cct ctt aaa gta tgt      432
Pro Ile Leu Lys Val Asp Leu Thr Pro His Ile Pro Leu Lys Val Cys
    130                 135                 140

gag tct aat aat att gct ggc ttt cca gag aga gaa ggg gaa ttg cgg      480
Glu Ser Asn Asn Ile Ala Gly Phe Pro Glu Arg Glu Gly Glu Leu Arg
```

-continued

```
145                 150                 155                 160

aga aca ggc cca aca gaa aca ctc ccc ttt gat gca ctg ccc cca gaa      528
Arg Thr Gly Pro Thr Glu Thr Leu Pro Phe Asp Ala Leu Pro Pro Glu
                165                 170                 175

aaa caa gaa gtt gca ttc gag                                          549
Lys Gln Glu Val Ala Phe Glu
            180


<210> SEQ ID NO 8
<211> LENGTH: 183
<212> TYPE: PRT
<213> ORGANISM: Tobacco vein mottling virus

<400> SEQUENCE: 8

Gly Lys Ser Arg Arg Arg Leu Gln Phe Arg Lys Ala Arg Asp Asp Lys
1               5                   10                  15

Met Gly Tyr Ile Met His Gly Glu Gly Asp Thr Ile Glu His Phe Phe
            20                  25                  30

Gly Ala Ala Tyr Thr Lys Lys Gly Lys Ser Lys Gly Lys Thr His Gly
        35                  40                  45

Ala Gly Thr Lys Ala His Lys Phe Val Asn Met Tyr Gly Val Ser Pro
    50                  55                  60

Asp Glu Tyr Ser Tyr Val Arg Tyr Leu Asp Pro Val Thr Gly Ala Thr
65                  70                  75                  80

Leu Asp Glu Ser Pro Met Thr Asp Leu Asn Ile Val Gln Glu His Phe
                85                  90                  95

Gly Glu Ile Arg Arg Glu Ala Ile Leu Ala Asp Ala Met Ser Pro Gln
            100                 105                 110

Gln Arg Asn Lys Gly Ile Gln Ala Tyr Phe Val Arg Asn Ser Thr Met
        115                 120                 125

Pro Ile Leu Lys Val Asp Leu Thr Pro His Ile Pro Leu Lys Val Cys
    130                 135                 140

Glu Ser Asn Asn Ile Ala Gly Phe Pro Glu Arg Glu Gly Glu Leu Arg
145                 150                 155                 160

Arg Thr Gly Pro Thr Glu Thr Leu Pro Phe Asp Ala Leu Pro Pro Glu
                165                 170                 175

Lys Gln Glu Val Ala Phe Glu
            180


<210> SEQ ID NO 9
<211> LENGTH: 576
<212> TYPE: DNA
<213> ORGANISM: Turnip mosaic virus
<220> FEATURE:
<221> NAME/KEY: CDS
<222> LOCATION: (1)..(576)

<400> SEQUENCE: 9

gct aaa ggc aag agg caa aga cag aaa ctg aag ttt cgc aac gcc cga       48
Ala Lys Gly Lys Arg Gln Arg Gln Lys Leu Lys Phe Arg Asn Ala Arg
1               5                   10                  15

gac aac aaa atg ggt agg gaa gtg tat gga gac gac gac acc ata gag       96
Asp Asn Lys Met Gly Arg Glu Val Tyr Gly Asp Asp Asp Thr Ile Glu
            20                  25                  30

cat ttc ttt gga gat gct tac aca aag aaa gga aag agc aaa ggc agg      144
His Phe Phe Gly Asp Ala Tyr Thr Lys Lys Gly Lys Ser Lys Gly Arg
        35                  40                  45

aca cgt ggc atc ggg cat aaa aac agg aag ttc atc aat atg tat ggg      192
Thr Arg Gly Ile Gly His Lys Asn Arg Lys Phe Ile Asn Met Tyr Gly
    50                  55                  60
```

```
ttt gat cct gaa gat ttc tct gca gtt agg ttc gta gat cca ctc aca      240
Phe Asp Pro Glu Asp Phe Ser Ala Val Arg Phe Val Asp Pro Leu Thr
65                  70                  75                  80

ggg gcg aca ata gat gaa aac cca ttc acg gac atc act ctt gtg caa      288
Gly Ala Thr Ile Asp Glu Asn Pro Phe Thr Asp Ile Thr Leu Val Gln
                85                  90                  95

aag cac ttt ggt gac ata aga atg gat ttg ctc gga gag gat gag ctg      336
Lys His Phe Gly Asp Ile Arg Met Asp Leu Leu Gly Glu Asp Glu Leu
            100                 105                 110

gac cca aat gag ata cga atg aac agg gca atc cag gcc tac tac atg      384
Asp Pro Asn Glu Ile Arg Met Asn Arg Ala Ile Gln Ala Tyr Tyr Met
        115                 120                 125

aac aat aaa aca ggc aag gct ctg aag gta gac ttg aca cca cac ata      432
Asn Asn Lys Thr Gly Lys Ala Leu Lys Val Asp Leu Thr Pro His Ile
    130                 135                 140

cct ctc aag gtg tgt gac ctt cat gca acc att gct gga ttc cca gag      480
Pro Leu Lys Val Cys Asp Leu His Ala Thr Ile Ala Gly Phe Pro Glu
145                 150                 155                 160

aga gag aat gaa ctg agg caa act gga aag gct cag cct atc agt ata      528
Arg Glu Asn Glu Leu Arg Gln Thr Gly Lys Ala Gln Pro Ile Ser Ile
                165                 170                 175

gat gaa gtg ccg aga gcc aac aac gaa ctc atc cca gtg gac cat gag      576
Asp Glu Val Pro Arg Ala Asn Asn Glu Leu Ile Pro Val Asp His Glu
            180                 185                 190


<210> SEQ ID NO 10
<211> LENGTH: 192
<212> TYPE: PRT
<213> ORGANISM: Turnip mosaic virus

<400> SEQUENCE: 10

Ala Lys Gly Lys Arg Gln Arg Gln Lys Leu Lys Phe Arg Asn Ala Arg
1               5                   10                  15

Asp Asn Lys Met Gly Arg Glu Val Tyr Gly Asp Asp Asp Thr Ile Glu
            20                  25                  30

His Phe Phe Gly Asp Ala Tyr Thr Lys Lys Gly Lys Ser Lys Gly Arg
        35                  40                  45

Thr Arg Gly Ile Gly His Lys Asn Arg Lys Phe Ile Asn Met Tyr Gly
    50                  55                  60

Phe Asp Pro Glu Asp Phe Ser Ala Val Arg Phe Val Asp Pro Leu Thr
65                  70                  75                  80

Gly Ala Thr Ile Asp Glu Asn Pro Phe Thr Asp Ile Thr Leu Val Gln
                85                  90                  95

Lys His Phe Gly Asp Ile Arg Met Asp Leu Leu Gly Glu Asp Glu Leu
            100                 105                 110

Asp Pro Asn Glu Ile Arg Met Asn Arg Ala Ile Gln Ala Tyr Tyr Met
        115                 120                 125

Asn Asn Lys Thr Gly Lys Ala Leu Lys Val Asp Leu Thr Pro His Ile
    130                 135                 140

Pro Leu Lys Val Cys Asp Leu His Ala Thr Ile Ala Gly Phe Pro Glu
145                 150                 155                 160

Arg Glu Asn Glu Leu Arg Gln Thr Gly Lys Ala Gln Pro Ile Ser Ile
                165                 170                 175

Asp Glu Val Pro Arg Ala Asn Asn Glu Leu Ile Pro Val Asp His Glu
            180                 185                 190


<210> SEQ ID NO 11
<211> LENGTH: 579
```

<212> TYPE: DNA
<213> ORGANISM: Lettuce mosaic virus
<220> FEATURE:
<221> NAME/KEY: CDS
<222> LOCATION: (1)..(579)

<400> SEQUENCE: 11

```
ggc aaa ggt aaa cgg caa aga cag aag ctt cgt tat cga caa gca agg       48
Gly Lys Gly Lys Arg Gln Arg Gln Lys Leu Arg Tyr Arg Gln Ala Arg
1               5                   10                  15

gat aat aag atg ggc att gaa gtt tat ggt gac gat gcg acg atg gaa       96
Asp Asn Lys Met Gly Ile Glu Val Tyr Gly Asp Asp Ala Thr Met Glu
            20                  25                  30

cac tat ttt gga gct gcg tac aca gag aaa gga aag aaa tcc gga aag      144
His Tyr Phe Gly Ala Ala Tyr Thr Glu Lys Gly Lys Lys Ser Gly Lys
        35                  40                  45

acg aaa gga atg ggg acg aaa aat cga aga ttt gtt aac atg tat ggg      192
Thr Lys Gly Met Gly Thr Lys Asn Arg Arg Phe Val Asn Met Tyr Gly
    50                  55                  60

tac aac cca gaa gat tac tcg ttc atc cga ttt ctg gac cca ctc aca      240
Tyr Asn Pro Glu Asp Tyr Ser Phe Ile Arg Phe Leu Asp Pro Leu Thr
65                  70                  75                  80

ggg aaa aca atg gat gaa caa gta ttc act gac ata agt ctc gtc caa      288
Gly Lys Thr Met Asp Glu Gln Val Phe Thr Asp Ile Ser Leu Val Gln
                85                  90                  95

gat gcc ttt ggt aaa gaa aga ctc aaa ctc ctg tcc gaa ggg gaa att      336
Asp Ala Phe Gly Lys Glu Arg Leu Lys Leu Leu Ser Glu Gly Glu Ile
            100                 105                 110

gag tca gag cac atg cga aat ggg att aga gct tat ctt gtc aag aat      384
Glu Ser Glu His Met Arg Asn Gly Ile Arg Ala Tyr Leu Val Lys Asn
        115                 120                 125

ctt acc aca gca gct ctc gaa ata gac atg acc cct cac aac tct tgc      432
Leu Thr Thr Ala Ala Leu Glu Ile Asp Met Thr Pro His Asn Ser Cys
    130                 135                 140

cag ctc gga acc aag aca aac aac ata gca gga ttt gta gac agg gag      480
Gln Leu Gly Thr Lys Thr Asn Asn Ile Ala Gly Phe Val Asp Arg Glu
145                 150                 155                 160

tac gaa ttg cgt caa acc ggg gaa gcc agg gtt gtt gct cca gca ctg      528
Tyr Glu Leu Arg Gln Thr Gly Glu Ala Arg Val Val Ala Pro Ala Leu
                165                 170                 175

att cca aaa gac aat cca atc acg gac gag gat att ccc gta aag cat      576
Ile Pro Lys Asp Asn Pro Ile Thr Asp Glu Asp Ile Pro Val Lys His
            180                 185                 190

gaa                                                                  579
Glu
```

<210> SEQ ID NO 12
<211> LENGTH: 193
<212> TYPE: PRT
<213> ORGANISM: Lettuce mosaic virus

<400> SEQUENCE: 12

```
Gly Lys Gly Lys Arg Gln Arg Gln Lys Leu Arg Tyr Arg Gln Ala Arg
1               5                   10                  15

Asp Asn Lys Met Gly Ile Glu Val Tyr Gly Asp Asp Ala Thr Met Glu
            20                  25                  30

His Tyr Phe Gly Ala Ala Tyr Thr Glu Lys Gly Lys Lys Ser Gly Lys
        35                  40                  45

Thr Lys Gly Met Gly Thr Lys Asn Arg Arg Phe Val Asn Met Tyr Gly
    50                  55                  60

Tyr Asn Pro Glu Asp Tyr Ser Phe Ile Arg Phe Leu Asp Pro Leu Thr
```

```
65                  70                  75                  80

Gly Lys Thr Met Asp Glu Gln Val Phe Thr Asp Ile Ser Leu Val Gln
                85                  90                  95

Asp Ala Phe Gly Lys Glu Arg Leu Lys Leu Leu Ser Glu Gly Glu Ile
            100                 105                 110

Glu Ser Glu His Met Arg Asn Gly Ile Arg Ala Tyr Leu Val Lys Asn
        115                 120                 125

Leu Thr Thr Ala Ala Leu Glu Ile Asp Met Thr Pro His Asn Ser Cys
    130                 135                 140

Gln Leu Gly Thr Lys Thr Asn Asn Ile Ala Gly Phe Val Asp Arg Glu
145                 150                 155                 160

Tyr Glu Leu Arg Gln Thr Gly Glu Ala Arg Val Val Ala Pro Ala Leu
                165                 170                 175

Ile Pro Lys Asp Asn Pro Ile Thr Asp Glu Asp Ile Pro Val Lys His
            180                 185                 190

Glu


<210> SEQ ID NO 13
<211> LENGTH: 162
<212> TYPE: DNA
<213> ORGANISM: Potato virus Y
<220> FEATURE:
<221> NAME/KEY: CDS
<222> LOCATION: (1)..(162)

<400> SEQUENCE: 13

agg aaa aag gga aaa ggt aaa ggt acc aca gtt ggt atg ggc aag tca       48
Arg Lys Lys Gly Lys Gly Lys Gly Thr Thr Val Gly Met Gly Lys Ser
1               5                   10                  15

agc agg agg ttc att aac atg tac ggg ttc gac cca aca gag tac tca       96
Ser Arg Arg Phe Ile Asn Met Tyr Gly Phe Asp Pro Thr Glu Tyr Ser
            20                  25                  30

ttc atc caa ttc gtt gat cca ctc act ggg gca caa ata gaa gag aat      144
Phe Ile Gln Phe Val Asp Pro Leu Thr Gly Ala Gln Ile Glu Glu Asn
        35                  40                  45

gtc tat gct gac att aga                                              162
Val Tyr Ala Asp Ile Arg
    50


<210> SEQ ID NO 14
<211> LENGTH: 54
<212> TYPE: PRT
<213> ORGANISM: Potato virus Y

<400> SEQUENCE: 14

Arg Lys Lys Gly Lys Gly Lys Gly Thr Thr Val Gly Met Gly Lys Ser
1               5                   10                  15

Ser Arg Arg Phe Ile Asn Met Tyr Gly Phe Asp Pro Thr Glu Tyr Ser
            20                  25                  30

Phe Ile Gln Phe Val Asp Pro Leu Thr Gly Ala Gln Ile Glu Glu Asn
        35                  40                  45

Val Tyr Ala Asp Ile Arg
    50


<210> SEQ ID NO 15
<211> LENGTH: 126
<212> TYPE: DNA
<213> ORGANISM: Potato virus Y
<220> FEATURE:
<221> NAME/KEY: CDS
<222> LOCATION: (1)..(126)
```

<400> SEQUENCE: 15

```
agg aaa aag gga aaa ggt aaa ggt acc aca gtt ggt atg ggc aag tca       48
Arg Lys Lys Gly Lys Gly Lys Gly Thr Thr Val Gly Met Gly Lys Ser
1               5                   10                  15

agc agg agg ttc att aac atg tac ggg ttc gac cca aca gag tac tca       96
Ser Arg Arg Phe Ile Asn Met Tyr Gly Phe Asp Pro Thr Glu Tyr Ser
            20                  25                  30

ttc atc caa ttc gtt gat cca ctc act ggg                              126
Phe Ile Gln Phe Val Asp Pro Leu Thr Gly
        35                  40
```

<210> SEQ ID NO 16
<211> LENGTH: 42
<212> TYPE: PRT
<213> ORGANISM: Potato virus Y

<400> SEQUENCE: 16

```
Arg Lys Lys Gly Lys Gly Lys Gly Thr Thr Val Gly Met Gly Lys Ser
1               5                   10                  15

Ser Arg Arg Phe Ile Asn Met Tyr Gly Phe Asp Pro Thr Glu Tyr Ser
            20                  25                  30

Phe Ile Gln Phe Val Asp Pro Leu Thr Gly
        35                  40
```

<210> SEQ ID NO 17
<211> LENGTH: 78
<212> TYPE: DNA
<213> ORGANISM: Potato virus Y
<220> FEATURE:
<221> NAME/KEY: CDS
<222> LOCATION: (1)..(78)

<400> SEQUENCE: 17

```
agg aaa aag gga aaa ggt aaa ggt acc aca gtt ggt atg ggc aag tca       48
Arg Lys Lys Gly Lys Gly Lys Gly Thr Thr Val Gly Met Gly Lys Ser
1               5                   10                  15

agc agg agg ttc att aac atg tac ggg ttc                               78
Ser Arg Arg Phe Ile Asn Met Tyr Gly Phe
            20                  25
```

<210> SEQ ID NO 18
<211> LENGTH: 26
<212> TYPE: PRT
<213> ORGANISM: Potato virus Y

<400> SEQUENCE: 18

```
Arg Lys Lys Gly Lys Gly Lys Gly Thr Thr Val Gly Met Gly Lys Ser
1               5                   10                  15

Ser Arg Arg Phe Ile Asn Met Tyr Gly Phe
            20                  25
```

<210> SEQ ID NO 19
<211> LENGTH: 57
<212> TYPE: DNA
<213> ORGANISM: Potato virus Y
<220> FEATURE:
<221> NAME/KEY: CDS
<222> LOCATION: (1)..(57)

<400> SEQUENCE: 19

```
agg aaa aag gga aaa ggt aaa ggt acc aca gtt ggt atg ggc aag tca       48
Arg Lys Lys Gly Lys Gly Lys Gly Thr Thr Val Gly Met Gly Lys Ser
1               5                   10                  15
```

```
                                                      -continued
agc agg agg                                                                57
Ser Arg Arg

<210> SEQ ID NO 20
<211> LENGTH: 19
<212> TYPE: PRT
<213> ORGANISM: Potato virus Y

<400> SEQUENCE: 20

Arg Lys Lys Gly Lys Gly Lys Gly Thr Thr Val Gly Met Gly Lys Ser
1               5                   10                  15

Ser Arg Arg

<210> SEQ ID NO 21
<211> LENGTH: 105
<212> TYPE: DNA
<213> ORGANISM: Potato virus Y
<220> FEATURE:
<221> NAME/KEY: CDS
<222> LOCATION: (1)..(105)

<400> SEQUENCE: 21

ttc att aac atg tac ggg ttc gac cca aca gag tac tca ttc atc caa         48
Phe Ile Asn Met Tyr Gly Phe Asp Pro Thr Glu Tyr Ser Phe Ile Gln
1               5                   10                  15

ttc gtt gat cca ctc act ggg gca caa ata gaa gag aat gtc tat gct        96
Phe Val Asp Pro Leu Thr Gly Ala Gln Ile Glu Glu Asn Val Tyr Ala
                20                  25                  30

gac att aga                                                            105
Asp Ile Arg
        35

<210> SEQ ID NO 22
<211> LENGTH: 35
<212> TYPE: PRT
<213> ORGANISM: Potato virus Y

<400> SEQUENCE: 22

Phe Ile Asn Met Tyr Gly Phe Asp Pro Thr Glu Tyr Ser Phe Ile Gln
1               5                   10                  15

Phe Val Asp Pro Leu Thr Gly Ala Gln Ile Glu Glu Asn Val Tyr Ala
                20                  25                  30

Asp Ile Arg
        35

<210> SEQ ID NO 23
<211> LENGTH: 25
<212> TYPE: DNA
<213> ORGANISM: Artificial
<220> FEATURE:
<223> OTHER INFORMATION: VPg gene PCR primer

<400> SEQUENCE: 23

gggggggatc catggggaaa ataaa                                             25

<210> SEQ ID NO 24
<211> LENGTH: 27
<212> TYPE: DNA
<213> ORGANISM: Artificial
<220> FEATURE:
<223> OTHER INFORMATION: VPg gene PCR primer

<400> SEQUENCE: 24

cccccagatc tctattattc atgctcc                                           27
```

<210> SEQ ID NO 25
<211> LENGTH: 129
<212> TYPE: DNA
<213> ORGANISM: Autographa californica nucleopolyhedrovirus

<400> SEQUENCE: 25
atcatggaga taattaaaat gataaccatc tcgcaaataa ataagtattt tactgttttc 60
gtaacagttt tgtaataaaa aaacctataa atattccgga ttattcatac cgtcccacca 120
tcgggcgcg 129

<210> SEQ ID NO 26
<211> LENGTH: 4
<212> TYPE: PRT
<213> ORGANISM: Artificial
<220> FEATURE:
<223> OTHER INFORMATION: VPg motif

<400> SEQUENCE: 26

Asn Met Tyr Gly
1

<210> SEQ ID NO 27
<211> LENGTH: 111
<212> TYPE: PRT
<213> ORGANISM: Feline calicivirus

<400> SEQUENCE: 27

Ala Lys Gly Lys Thr Lys Ser Lys Val Gly Pro Tyr Arg Gly Arg Gly
1 5 10 15

Val Ala Leu Thr Asp Asp Glu Tyr Asp Glu Trp Arg Glu His Asn Ala
20 25 30

Thr Arg Lys Leu Asp Leu Ser Val Glu Asp Phe Leu Met Leu Arg His
35 40 45

Arg Ala Ala Leu Gly Ala Asp Asp Ala Asp Ala Val Lys Phe Arg Ser
50 55 60

Trp Trp Asn Ser Arg Ser Arg Leu Ala Asp Asp Tyr Glu Asp Val Thr
65 70 75 80

Val Ile Gly Lys Gly Gly Val Lys His Glu Lys Ile Arg Thr Asn Thr
85 90 95

Leu Arg Ala Val Asp Arg Gly Tyr Asp Val Ser Phe Ala Glu Glu
100 105 110

<210> SEQ ID NO 28
<211> LENGTH: 132
<212> TYPE: PRT
<213> ORGANISM: Human calicivirus

<400> SEQUENCE: 28

Gly Lys Lys Gly Lys Asn Lys Thr Gly Arg Gly Lys Lys His Thr Ala
1 5 10 15

Phe Ser Ser Lys Gly Leu Ser Asp Glu Glu Tyr Asp Glu Tyr Lys Arg
20 25 30

Ile Arg Glu Glu Arg Asn Gly Lys Tyr Ser Ile Glu Glu Tyr Leu Gln
35 40 45

Asp Arg Asp Lys Tyr Tyr Glu Glu Val Ala Ile Ala Arg Ala Thr Glu
50 55 60

Glu Asp Phe Cys Glu Glu Glu Glu Ala Lys Ile Arg Gln Arg Ile Phe
65 70 75 80

Arg Pro Thr Arg Lys Gln Arg Lys Glu Glu Arg Ala Ser Leu Gly Leu

```
                85                  90                  95

Val Thr Gly Ser Glu Ile Arg Lys Arg Asn Pro Asp Asp Phe Lys Pro
            100                 105                 110

Lys Gly Lys Leu Trp Ala Asp Asp Asp Arg Ser Val Asp Tyr Asn Glu
        115                 120                 125

Lys Leu Asp Phe
    130


<210> SEQ ID NO 29
<211> LENGTH: 138
<212> TYPE: PRT
<213> ORGANISM: Human calicivirus

<400> SEQUENCE: 29

Gly Lys Asn Lys Gly Lys Thr Lys Lys Gly Arg Gly Arg Lys Asn Asn
1               5                   10                  15

Tyr Asn Ala Phe Ser Arg Arg Gly Leu Ser Asp Glu Glu Tyr Glu Glu
            20                  25                  30

Tyr Lys Lys Ile Arg Glu Glu Lys Asn Gly Asn Tyr Ser Ile Gln Glu
        35                  40                  45

Tyr Leu Glu Asp Arg Gln Arg Tyr Glu Glu Glu Leu Ala Glu Val Gln
    50                  55                  60

Ala Gly Gly Asp Gly Gly Ile Gly Glu Thr Glu Met Glu Ile Arg His
65                  70                  75                  80

Arg Val Phe Tyr Lys Ser Lys Ser Lys Lys His Gln Gln Glu Gln Arg
                85                  90                  95

Arg Gln Leu Gly Leu Val Thr Gly Ser Asp Ile Arg Lys Arg Lys Pro
            100                 105                 110

Ile Asp Trp Thr Pro Pro Lys Asn Glu Trp Ala Asp Asp Asp Arg Glu
        115                 120                 125

Val Asp Tyr Asn Glu Lys Ile Asn Phe Glu
    130                 135


<210> SEQ ID NO 30
<211> LENGTH: 124
<212> TYPE: PRT
<213> ORGANISM: Murine norovirus

<400> SEQUENCE: 30

Gly Lys Lys Gly Lys Asn Lys Lys Gly Arg Gly Arg Pro Gly Val Phe
1               5                   10                  15

Arg Thr Arg Gly Leu Thr Asp Glu Glu Tyr Asp Glu Phe Lys Lys Arg
            20                  25                  30

Arg Glu Ser Arg Gly Gly Lys Tyr Ser Ile Asp Asp Tyr Leu Ala Asp
        35                  40                  45

Arg Glu Arg Glu Glu Glu Leu Leu Glu Arg Asp Glu Glu Glu Ala Ile
    50                  55                  60

Phe Gly Asp Gly Phe Gly Leu Lys Ala Thr Arg Arg Ser Arg Lys Ala
65                  70                  75                  80

Glu Arg Ala Lys Leu Gly Leu Val Ser Gly Gly Asp Ile Arg Ala Arg
                85                  90                  95

Lys Pro Ile Asp Trp Asn Val Val Gly Pro Ser Trp Ala Asp Asp Asp
            100                 105                 110

Arg Gln Val Asp Tyr Gly Glu Lys Ile Asn Phe Glu
        115                 120


<210> SEQ ID NO 31
```

-continued

```
<211> LENGTH: 7
<212> TYPE: PRT
<213> ORGANISM: Artificial Sequence
<220> FEATURE:
<223> OTHER INFORMATION: eIF4E-binding motif
<220> FEATURE:
<221> NAME/KEY: MISC_FEATURE
<222> LOCATION: (2)..(5)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be Leu, Met or Phe

<400> SEQUENCE: 31

Tyr Xaa Xaa Xaa Xaa Leu Xaa
1               5
```